(12) United States Patent
Steinmetzer et al.

(10) Patent No.: US 9,133,194 B2
(45) Date of Patent: Sep. 15, 2015

(54) CYCLIC TRIPEPTIDE MIMETICS AS PLASMIN INHIBITORS

(76) Inventors: Torsten Steinmetzer, Jena (DE); Sebastian Saupe, Kaltennordheim (DE)

( * ) Notice: Subject to any disclaimer, the term of this patent is extended or adjusted under 35 U.S.C. 154(b) by 0 days.

(21) Appl. No.: 14/131,007

(22) PCT Filed: Jul. 9, 2012

(86) PCT No.: PCT/EP2012/063363
§ 371 (c)(1),
(2), (4) Date: Apr. 9, 2014

(87) PCT Pub. No.: WO2013/004845
PCT Pub. Date: Jan. 10, 2013

(65) Prior Publication Data
US 2014/0213781 A1    Jul. 31, 2014

(30) Foreign Application Priority Data
Jul. 7, 2011    (EP) ..................................... 11173132

(51) Int. Cl.
| | | |
|---|---|---|
| *A61K 38/00* | (2006.01) | |
| *C07K 16/00* | (2006.01) | |
| *C07D 471/06* | (2006.01) | |
| *C07K 5/065* | (2006.01) | |
| *A61K 38/06* | (2006.01) | |
| *A61K 38/12* | (2006.01) | |

(52) U.S. Cl.
CPC .......... *C07D 471/06* (2013.01); *C07K 5/06078* (2013.01); *A61K 38/06* (2013.01); *A61K 38/12* (2013.01)

(58) Field of Classification Search
None
See application file for complete search history.

(56) References Cited

FOREIGN PATENT DOCUMENTS

| WO | 2008/049595 | 5/2008 |
|---|---|---|
| WO | WO 2008049595 A1 * | 5/2008 |
| WO | 2012/004678 | 1/2012 |

OTHER PUBLICATIONS

Merck Manual Colorectal Cancer accessed Aug. 21, 2014 at URL merckmanuals.com/home/digestive_disorders/tumors_of_the_digestive_system/colorectal_cancer.html).*
Overview of Leukemia at URL merckmanuals.com/home/blood_disorders/leukemias/overview_of_leukemia.html?qt=Leukemia &alt=sh accessed Aug. 20, 2014).*
National Institute of Cancer—understanding and related topics, accessed Aug. 21, 2014 at URL: cancer.gov/cancertopics/understandingcancer.*
(Merck Manuals Brain Tumors accessed Aug. 21, 2014 at URL merckmanuals.com/home/brain_spinal_cord_and_nerve_disorders/tumors_of_the_nervous_system/brain_tumors.html).*
Merck Manual Breast Cancer accessed Aug. 21, 2014 at URL: merckmanuals.com/home/womens_health_issues/breast_disorders/breast_cancer.html).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh.*
Ovarian Cancer, accessed Aug. 21, 2014 at merckmanuals.com/home/womens_health_issues/cancers_of_the_female_reproductive_system/ovarian_cancer.html?qt=ovarian. cancer&alt=sh.*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html.*
Merck Manual Cancer of the Uterus, accessed Aug. 21, 2014 at URL: merckmanuals.com/home/womens_health_issues/cancers_of_the_female_reproductive_system/cancer_of_the_uterus.html?qt=Cancer of the Uterus&alt=sh.*
Comeau, The blood loss Analyzer—a new way to estimate blood loss, New Techniques, Journal of the American Association of Nurse Anesthetists, Feb. 1983, p. 81-84).*
Dano, Plasminogen Activation and Cancer, 2005 Schattauer GmbH, Stuttgart, 2005.*

* cited by examiner

*Primary Examiner* — James H Alstrum Acevedo
*Assistant Examiner* — Jeanette Lieb
(74) *Attorney, Agent, or Firm* — Clark & Brody

(57) ABSTRACT

The invention relates to peptide mimetics comprising the residues P4-P3-P2-P1, which were cyclized between the side chains of P3 and P2 amino acid and are, as inhibitors of the serine protease plasmin, suitable to be used to inhibit fibrinolysis and thus to reduce blood loss in hyperfibrinolytic conditions, for example during surgery.

18 Claims, No Drawings

CYCLIC TRIPEPTIDE MIMETICS AS PLASMIN INHIBITORS

The invention concerns N-terminally modified cyclic tripeptide mimetics which are, as inhibitors of the serine protease plasmin, suitable to be used to inhibit fibrinolysis and to reduce blood loss during surgery.

Introduction and State of the Art

Plasmin is a trypsin-like serine protease which cleaves peptide and protein substrates C-terminally of the basic amino acids arginine or lysine. Plasmin is generated from the zymogen plasminogen by catalytic action of the plasminogen activators urokinase or tPA. Among the substrates of plasmin count different proteins of the extracellular matrix and basal membrane, for example fibronectin, laminin, type IV-collagen or fibrin, but also numerous zymogens like proforms of matrix-metalloproteases or the plasminogen-activator urokinase. In the blood, plasmin is above all responsible for fibrinolysis by cleaving fibrin into soluble products.

Under certain pathological conditions, a spontaneous activation of fibrinolysis may occur. In the case of such a hyperplasminemia, not only the wound-closing fibrin is degraded, but in addition anticoagulant fibrinogen degradation products are synthesized. In this case, severe hemostatic disorders may result. Plasmin probably also plays an important role in rheumatoid arthritis since it is involved in the degradation of joint cartilage and matrix proteins (Li et al., Am. J. Pathology 2005, 166, 783-792). Plasmin is furthermore described as important activator of numerous inactive precursor forms of proteases and of angiogenesis or other growth factors which promote tumor formation and metastasis. Described was also a function of plasmin in proliferative vitreoretinopathy (PVR) via a plasmin-catalyzed activation of PDFG-C (platelet-derived growth factor C, Lei et al., Investigative Ophthalmology & Visual Science, January 2008, 49, 42-48). PVR may lead to retinal detachment in the eye and is one the main complications of surgeries on the retina in the eye.

Meanwhile several clinical studies exist with respect to the utilization of plasmin for thrombolytic therapy after cardiac infarction (Marder et al., *Stroke*. 2010, 41, Suppl. 1 S45-S49). As in the case of a thrombolytic therapy with plasminogen activators (urokinase, tPA, streptokinase), bleeding complications may also occur if plasmin is used which require a suitable antidote, for example an efficient plasmin inhibitor.

As antifibrinolytic agent, synthetic amino carboxylic acids such as ε-aminocaproic acid, p-aminomethylbenzoic acid or tranexaminic acid (trans-4-(aminomethyl)-cyclohexanecarboxylic acid, according to the new nomenclature tranexamic acid) are clinically used. These compounds block the binding of the zymogen plasminogen to fibrin and inhibit its activation to plasmin. These compounds consequently represent no direct inhibitors of plasmin and are not able to inhibit the activity of already formed plasmin. Orally administered tranexamic acid (Lysteda®) is used in the USA also for the treatment of heavy menstrual bleeding. These compounds may also be used for the prevention or alleviation of bleedings during tooth extraction or bleeding gums, especially in patients suffering from hemophilia. Basically all substances which inhibit plasmin either directly or which prevent its formation can also be used to treat mild forms of hemophilia.

As another antifibrinolytic agent, aprotinin (Trasylol®) was utilized, a polypeptide consisting of 58 amino acids which is derived from bovine lung tissue. Aprotinin inhibits plasmin with an inhibition constant of 1 nM, but this substance is relatively unspecific and also inhibits for example trypsin (K=0.1 nM) and plasma kallikrein ($K_i$=30 nM) effectively. A main application of aprotinin served the purpose to reduce blood loss, especially during cardiac surgery with cardiopulmonary bypass (CPB), which substantially reduced the need for perioperative blood transfusions (Sodha et al., Expert Rev. Cardiovasc. Ther. 2006, 4, 151-160). Aprotinin is also used as additive in fibrin adhesives. The use of aprotinin however is associated with several disadvantages. Since this substance is isolated from bovine organs, in principle the risk of pathogenic contaminations and allergic reactions exists. The risk of an anaphylactic shock is comparably low (<0.1%) when aprotinin is applied for the first time, increases however on repeated administration to 4-5% within 200 days. Some time ago it was reported that the administration of aprotinin in direct comparison with ε-aminocaproic acid or tranexamic acid induces an increased number of side effects (Mangano et al., New Engl. J. Med. 2006, 354, 353-365). The administration of aprotinin resulted in a doubling of the number of cases of kidney damage requiring subsequent dialysis. Furthermore, the risk of myocardial infarction and apoplectic stroke increased after administration of aprotinin as compared to the control groups. For these reasons, aprotinin was withdrawn from the market as far as possible in the year 2008.

Until now, only a relatively small number of synthetic plasmin inhibitors were developed. Sanders and Seto (J. Med. Chem. 1999, 42, 2969-2976) reported weakly effective 4-heterocyclohexanone derivates with inhibition constants ≥50 µM for plasmin. Xue and Seto reported on peptidic cyclohexanone derivatives with $IC_{50}$-values ≥2 µM (J. Med. Chem. 2005, 48, 6908-6917). Okada and Tsuda synthesized derivatives with a 4-aminomethylcyclohexanoyl residue which inhibit plasmin with $IC_{50}$-values of ≥0.1 µM (Okada et al., Chem. Pharm. Bull. 2000, 48, 1964-1972; Tsuda et al., Chem. Pharm. Bull. 2001, 49, 1457-1463). Effective plasmin inhibitors were recently described in WO 2008/049595 and by Dietrich et al. (Anesthesiology 2009, 110, 123-130), but some of the derivatives mentioned here are also inhibitors of other trypsin-like serine proteases like for example the coagulation factors factor Xa, thrombin or protein Ca.

In the case of selectivity investigations during the development of thrombin or factor Xa inhibitors, also inhibition constants for plasmin were specified for some of these derivatives. The thrombin inhibitor melagatran for example inhibits plasmin with a $K_i$-value of 0.7 µM (Gustafsson et al., Thromb. Haemost. 1998, 79, 110-118), while the structurally closely related compound H317/86 has an inhibition constant of 0.22 µM. Both compounds however inhibit the protease thrombin substantially more strongly with $K_i$-values≤2 nM.

As already described by way of introduction, plasmin belongs to the group of trypsin-like serine proteases with approx. 70 other representatives. The large number of structurally similar proteases complicates the development of selective substrate-analog inhibitors. Many of these serine proteases possess characteristically shaped pockets which are responsible for the specific binding of certain amino acid residues of the substrates and thus contribute to the affinity of substrate-analog inhibitors. In many trypsin-like serine proteases, the amino acid at position 99 (the numbering is based on the sequence of chymotrypsinogen) influences the size of the S2 pocket (binding pockets were defined according to Schechter and Berger, Biochem. Biophys. Res. Comm. 27, 157-162) and specifically distinguishes this pocket from other binding pockets. In the case of plasmin, residue 99 and a few neighboring residues are even entirely missing. The active center of plasmin is consequently more or less open and freely accessible for many substrates. For this reason, plasmin probably exhibits low substrate specificity and is able to cleave many different substrates.

Aim

Aim of the present invention is to provide synthetic active agents suitable for therapeutic application which inhibit, in analogy to aprotinin, plasmin in an efficient manner and which are thus suitable to be used for hemostasis in various applications, for example during surgical interventions and especially during cardiac surgery with cardiopulmonary bypasses (CBP) or during organ transplants. These compounds may also be used for the treatment of heavy menstrual bleeding and the prevention or alleviation of bleedings during tooth extraction or bleeding gums, especially in patients suffering from hemophilia. All active substances which inhibit plasmin either directly can in principle also be used for the therapy of mild forms of hemophilia or for the treatment of cancer and metastasis, if plasmin is involved in these pathophysiological processes.

Solution of the Problem

We surprisingly found that with cyclized tripeptide mimetics according to the general formula (I)

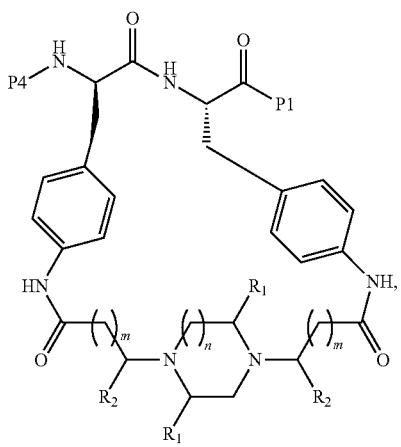

(I)

easily soluble, effective and selective plasmin inhibitors are obtained. The ring structure is generated by acylation using a suitable, substituted piperazine linker derivative between the side chains of the d-4-aminophenylalanine in P3 position and the 4-aminophenylalanine in P2 position of substrate-analog inhibitors of trypsin-like serine proteases (definition of P2- and P3 amino acids according to Schechter and Berger, Biochem. Biophys. Res. Comm. 27, 157-162).

Compounds of the general formula (I) may also be present as salt or as prodrug of said compounds, characterized in that n equals 1 or 2, and m equals 0, 1 or 2, and $R_1$ is either H or a branched or unbranched alkyl having up to 3 carbon atoms, and $R_2$ is either H or a branched or unbranched alkyl having up to 5 carbon atoms or an aryl or aralkyl group with up to 7 carbon atoms, and P1 is one of the following groups:

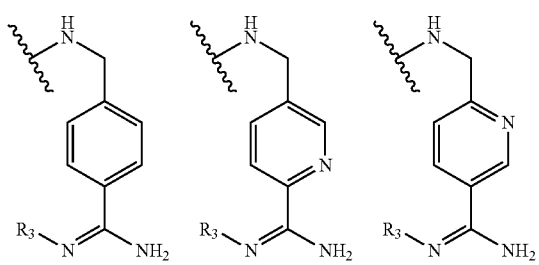

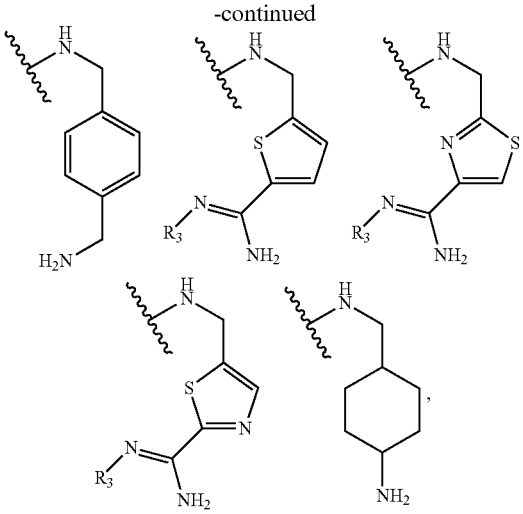

wherein $R_3$ is H, OH, O—$CH_3$, $NH_2$, O—CO—$CH_3$ or CO—O—$(CH_2)_z$—$CH_3$, and z is an integer of from 1 to 5, and P4 is either H, $SO_2$—$R_4$, $SO_2$—$NH_2$, $SO_2$—NH—$R_4$, $SO_2$—$N(R_4)_2$, CO—O—$R_4$, CO—$R_4$, $CH_2$—COOH, or $CH_2$—COOEt, wherein $R_4$ can be a branched or unbranched or cyclic alkyl group with 1 to 10 carbon atoms, or an aryl, a heteroaralkyl or aralkyl group with 6 to 10 carbon atoms, wherein the heteroaralkyl group may contain 1 to 3 heteroatoms chosen from N, S, or O, and wherein said alkyl, aryl, aralkyl and heteroaralkyl group can, if applicable, be substituted with 1 to 2 residues in arbitrary position which are chosen from the group of aminomethylene, cyano, $CF_3$, tetrazole, F, Cl, Br, COOH, COOEt, COOMe, methoxy, ethoxy, isopropoxy, methyl, ethyl, or isopropyl, and wherein the compound according to formula (I) is not

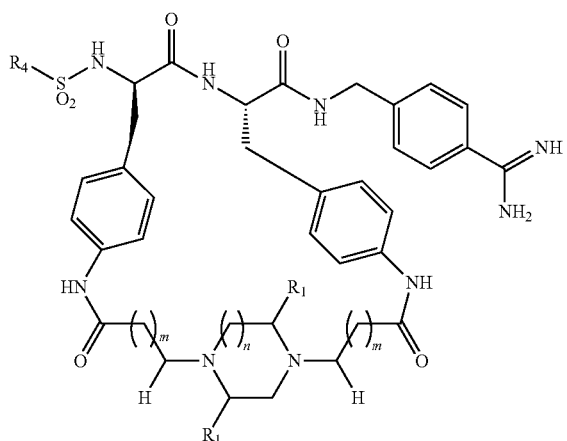

with $R_1$, $R_4$, m, and n as defined above.

Preferred compounds of the general formula (I) are characterized in that $R_1$ is H.

Other preferred compounds of the general formula (I) are characterized in that $R_2$ is H.

Other preferred compounds of the general formula (I) are characterized in that P4 is H, $SO_2$—$NH_2$ or one of the following structures:

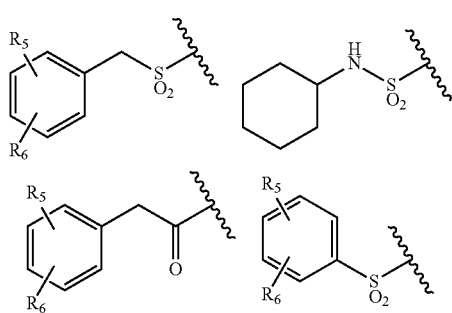

wherein $R_5$ and $R_6$ are, independently of one another, either H or aminomethylene, cyano, $CF_3$, tetrazole, F, Cl, Br, COOH, COOEt, COOMe, methoxy, ethoxy, isopropoxy, methyl, ethyl, or isopropyl, preferred is that $R_5$ and $R_6$ is H.

Other preferred compounds of the general formula (I) are characterized in that P1 is

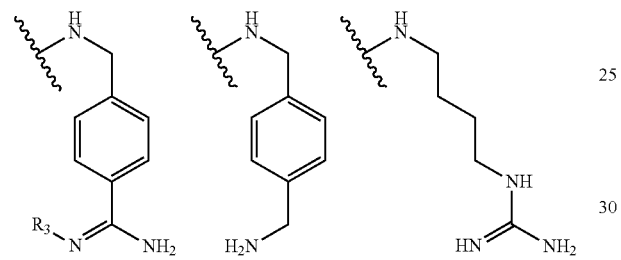

whereby $R_3$ is defined as before, but preferably is H.

Other preferred compounds of the general formula (I) are characterized in that m equals 0 or 1.

Particularly effective inhibitors according to the general formula (I) possess the following structures:

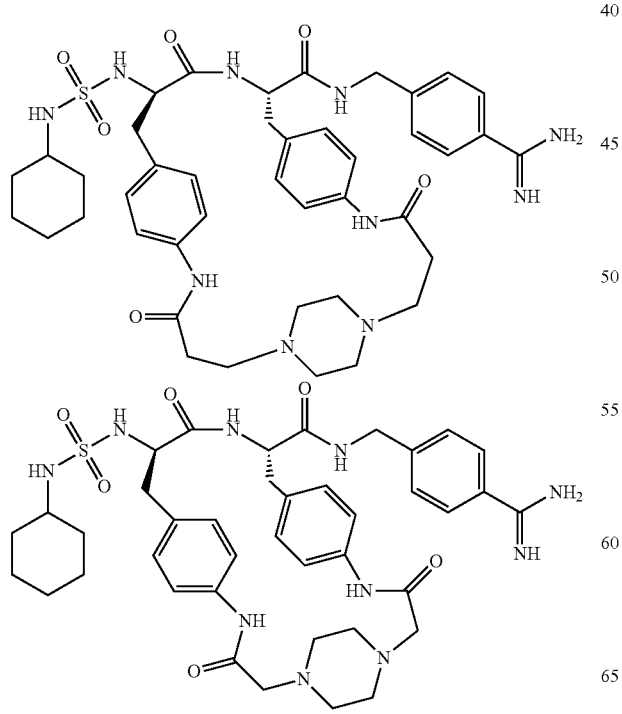

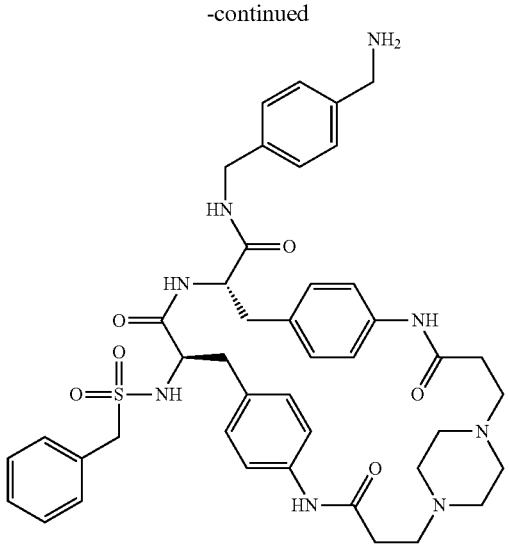

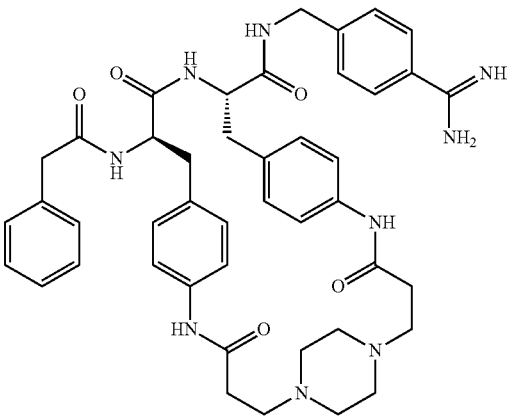

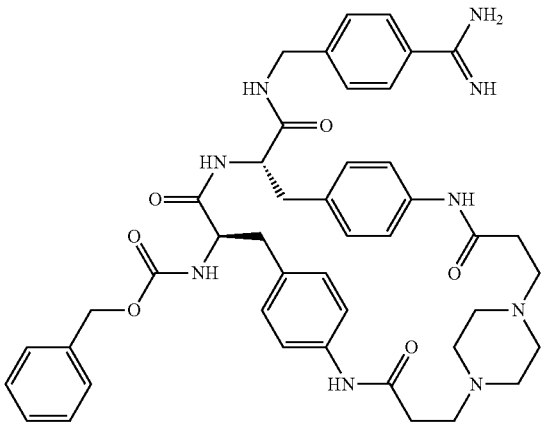

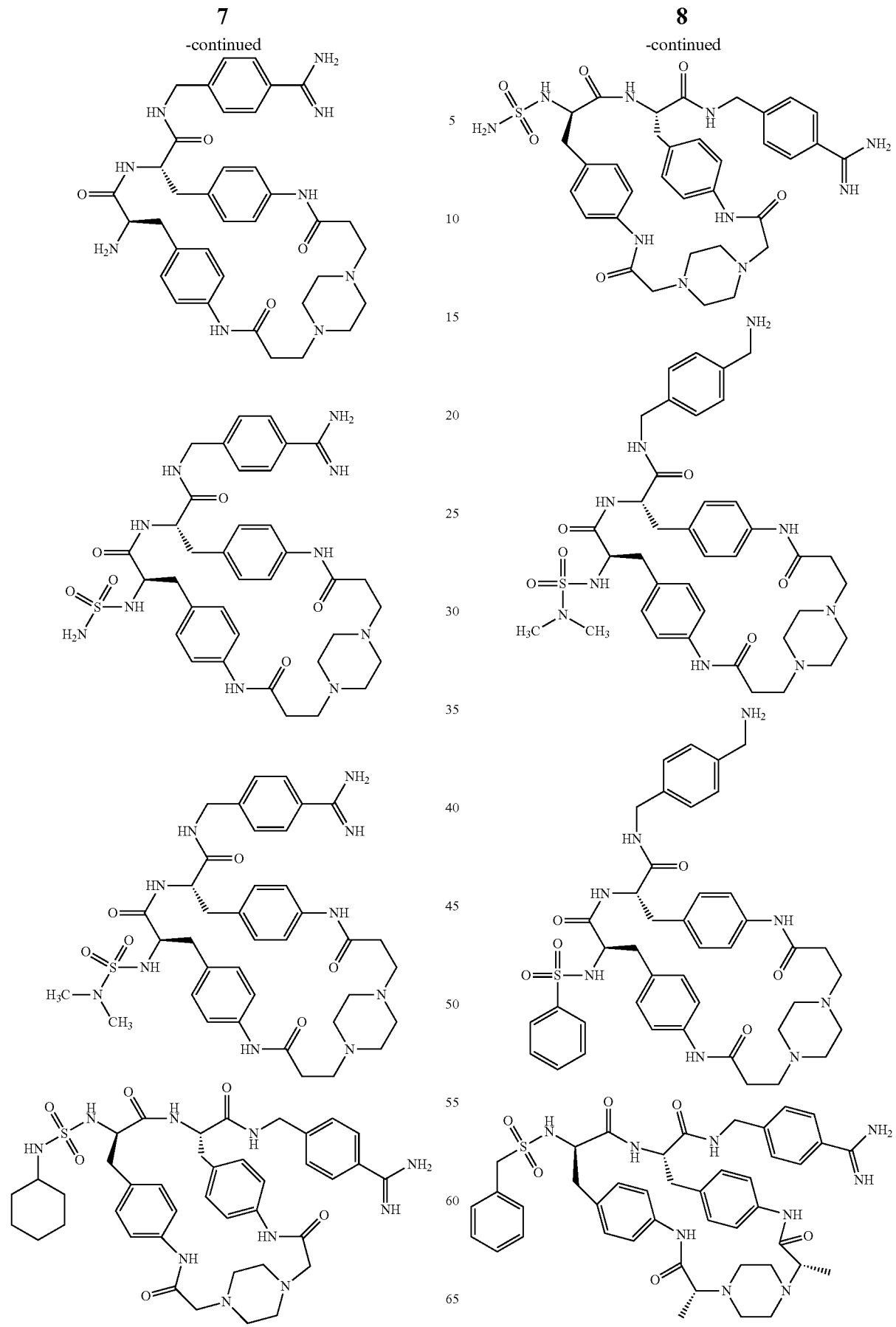

| 9 | 10 |
|---|---|
| -continued | -continued |
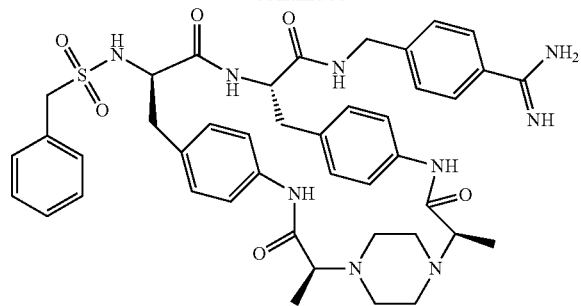
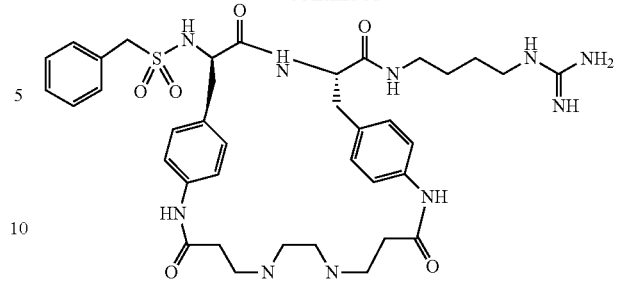
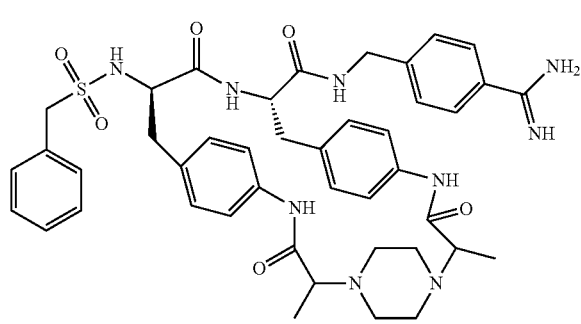
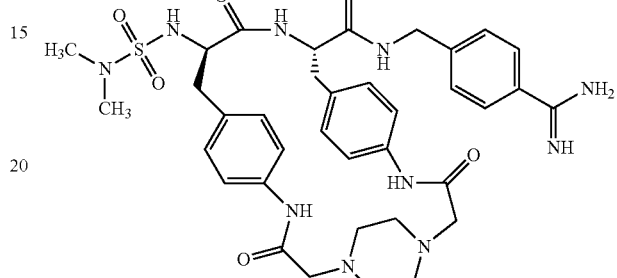
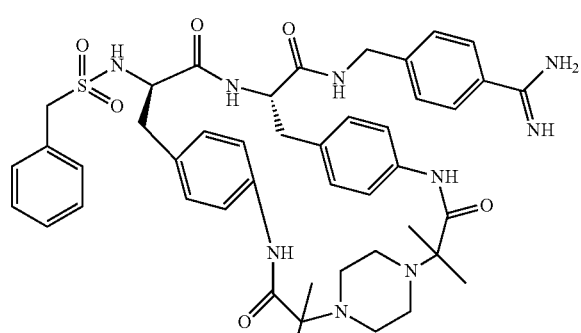
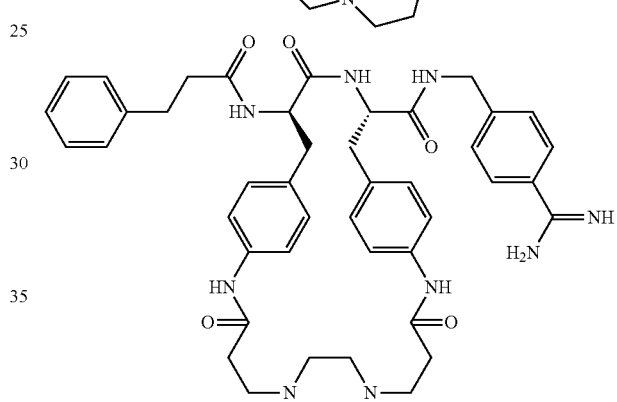
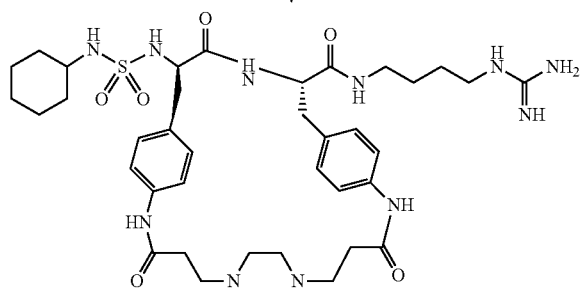
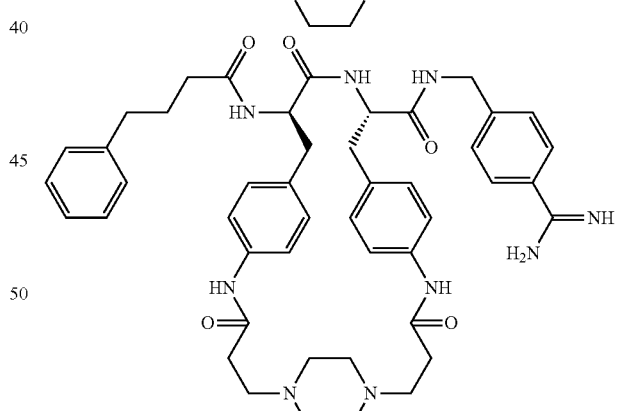
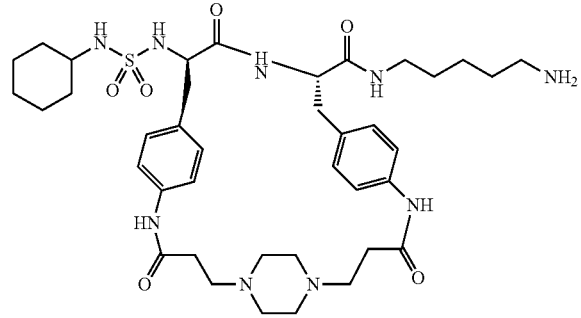
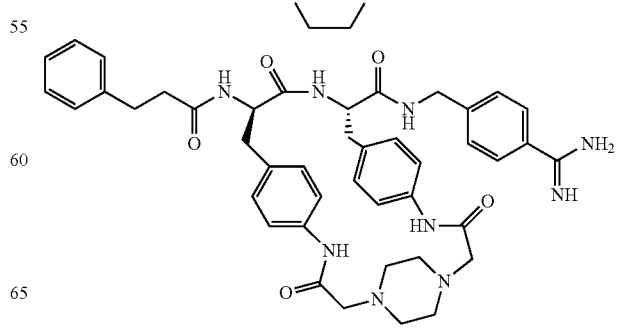

-continued

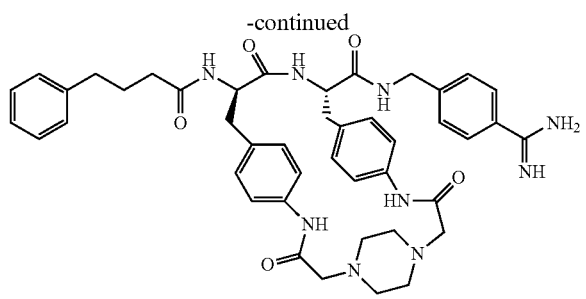

wherein the basic and, where applicable, existing acidic groups are present in physiologically compatible salt form.

Inhibitors of the general formula (I) may be used as drugs, either in the form of a tablet, a dragee, a capsule, a pellet, a suppository, a solution, in particular an injection or infusion solution, in the form of eye, nose, or ear drops, a juice, an emulsion or suspension, a globule, a styli, an aerosol, an aerosol spray, a powder, a paste, a cream or an ointment. Particularly preferred are however infusion and injection solutions.

These drugs can be used to reduce the blood loss in the case of hyperfibrinolytic conditions. They are particularly suitable to prevent the loss of blood during surgical procedures, in particular during heart surgery and organ transplants. The consumption of stored blood can thus be reduced.

The compounds of the general formula (I) may also be used as additive for the fabrication of fibrin adhesives.

The compounds of the general formula (I) may also be used as drugs for the treatment of cancer or for an inhibition of metastasis.

A further application of said plasmin inhibitors is the treatment of proliferative vitreoretinopathy (PVR), or their use as antidote for thrombolytic therapy with plasmin or plasminogen activators in the case that severe bleeding occurs.

The compounds of the general formula (I) may not only be used as drugs for the treatment of humans, but also in animals e.g. for the reduction of blood loss during surgery, in particular during heart surgery and organ transplants, for the fabrication of fibrin adhesives or the treatment of cancer or the inhibition of metastasis.

The compounds of the general formula (I) can also be used in in vitro applications for an inhibition of the serine protease plasmin, for example for diagnostic purposes or biochemical investigations.

The invention also includes pharmaceutically suitable or acceptable salts of compounds of the formula (I). These salts must have a pharmaceutically acceptable anion or cation. Suitable pharmaceutically acceptable acid addition salts of compounds of the present invention are e.g. salts of inorganic acids such as hydrochloric acid, hydrobromic, phosphoric, metaphosphoric, nitric, sulfonic, and sulfuric acid or organic acids such as e.g. acetic acid, benzenesulfonic, benzoic, citric, ethanesulfonic, fumaric, gluconic, glycolic, isethionic, lactic, lactobionic, maleic, methanesulfonic, succinic, p-toluene sulfonic, tartaric and trifluoroacetic acid. For medical purposes, particularly preferably the chlorine or acetate salt is used. Suitable pharmaceutically acceptable basic salts are e.g. ammonium salts, alkali metal salts (like sodium and potassium salts) and alkaline earth salts (like magnesium and calcium salts). Salts with a pharmaceutically non-acceptable anion also belong to the scope of the invention as useful intermediates for the preparation or purification of pharmaceutically acceptable salts and/or for use in non-therapeutic applications, for example in vitro applications.

The term "physiologically functional derivative" used in the following refers to any physiologically compatible derivative of a compound of the formula (I) according to this invention, e.g. an ester which upon administration to a mammal like e.g. humans is able to form (directly or indirectly) a compound of formula (I) or an active metabolite thereof. The physiologically functional derivatives include also prodrugs of the inventive compounds. Such prodrugs can be metabolized in vivo into a compound of the present invention. These prodrugs may themselves be active or not. Suitable prodrugs for benzamidine groups are for example compounds in which the amidine is present as hydroxyamidine, methoxyamidine, acetyl hydroxyamidine, alkoxycarbonylamidine, especially as hexyloxycarbonylamidine.

The compounds of this invention may also exist in different polymorphic forms, e.g. as amorphous and crystalline polymorphic forms and are a further aspect of the invention.

In the following, all references refer to compounds according to formula (I) as described above, as well as salts, solvates and physiologically functional derivatives thereof as described herein.

The present invention also relates to the use of compounds of formula (I) as inhibitors of plasmin. Also a pharmaceutical composition comprising a compound of formula (I) is object of this invention. The amount of the compound according to formula (I) which is required to achieve the desired biological effect depends on a variety of factors, e.g. the specific compound chosen, the intended use thereof, the mode of administration, and the clinical condition of the patient.

In general, the daily dose is in a range of 0.03 mg to 1000 mg (typically in the range of 3 mg to 100 mg) per day per kilogram of bodyweight, for example 3-10 mg/kg/day. An intravenous dose may e.g. range from 0.03 mg to 3.0 mg/kg, which can suitably be administered as infusion of 10 ng to 100 μg per kilogram per minute. Suitable infusion solutions for these purposes may contain e.g. from 0.1 ng to 10 mg, typically from 1 ng to 10 mg per milliliter. Single doses may contain e.g. from 1 mg to 3 g of the active substance. Thus, ampoules for injections may for example contain from 1 mg to 100 mg, and orally administrable single dosage formulations like e.g. tablets or capsules for example from 1.0 to 1000 mg, typically from 10 to 600 mg. In the case of pharmaceutically acceptable salts, the aforementioned weight specifications refer to the weight of the free compound which the salt is derived from. For the prophylaxis or therapy of the abovementioned conditions, compounds of the formula (I) may be used themselves as compound, but they are preferably present in the form of a pharmaceutical composition with a compatible carrier or excipient. The carrier and/or excipient must be naturally acceptable in the sense that it is compatible with other ingredients of the composition and not harmful to the health of the patient.

The carrier may be a solid, a liquid, or both and is preferably formulated with the compound as single dose, for example as tablet which may contain from 0.05% to 95% by weight of the active substance. Further pharmaceutically active substances may also be present, including further compounds according to formula (I). The pharmaceutical compositions of this invention can be prepared according to one of the known pharmaceutical procedures which consist basically of mixing the components with pharmacologically acceptable carriers and/or excipients. Inventive pharmaceutical compositions are in particular those which are suitable for oral, rectal, topical, peroral (e.g. sublingual) and parenteral (e.g. subcutaneous, intramuscular, intradermal or intravenous) administration, although the most suitable mode of administration in each individual case depends on the nature and severity of the condition to be treated and on the kind of compound according to formula (I) being used. Also aerosols are suitable pharmaceutical compositions for compounds of this invention, which are also in the form of aerosol sprays particularly suitable for the treatment and prophylaxis of disorders of the respiratory tract. Also coated formulations and coated controlled-release formulations are within the scope of the invention. Preferred are acid-resistant and enteric formulations. Suitable enteric coatings comprise cellulose acetate phthalate, polyvinyl acetate phthalate, hydroxypropyl methylcellulose phthalate and anionic polymers of methacrylic acid and methyl methacrylate.

Suitable pharmaceutical compounds for oral administration can be present as separate units like for example capsules, cachets, lozenges or tablets each containing a certain amount of the compound according to formula (I); as powder or granulates; as solution or suspension in an aqueous or non-aqueous liquid; or as oil-in-water or water-in-oil emulsion. These compositions may, as already mentioned, be prepared using any suitable pharmaceutical method which includes a step in which the active substance and the carrier (which may consist of one or more additional components) are brought into contact. In general, the compositions are prepared by uniform and homogeneous mixing of the active substance with a liquid and/or finely distributed solid carrier, after which the product is shaped, if required.

A tablet can for example be prepared by pressing or forming a powder or granulate, if required mixed with one or more additional components. Compressed tablets can be prepared by tableting the compound in free-flowing form like for example a powder or granulate in a suitable machine, if required mixed with a binding agent, lubricant, inert filler and/or one (or more) surface-active/dispersing agents. Molded tablets can be prepared by molding the powdery compound which is moistened with inert liquid filler in a suitable machine.

Pharmaceutical compositions which are suitable for per-oral (sublingual) administration comprise lozenges which contain a compound according to formula (I) with a flavoring, usually sucrose or gum arabic or tragacanth, and pastilles, which include an administration of an inert base such as gelatin and glycerol or sucrose and acacia gum.

Suitable pharmaceutical compositions for parenteral administration comprise preferably sterile aqueous preparations of a compound of formula (I) which are preferably isotonic with the blood of the intended recipient. These preparations are preferably administered intravenously, although administration may also be performed subcutaneously, intramuscularly or intradermally as injection.

These preparations can preferably be prepared by mixing the compound with water. The resulting solution is sterilized and made isotonic with the blood. Injectable compositions according to the invention generally contain from 0.1 to 5% by weight of the active compound.

Regarding the further formulation, it is referred to common manuals.

The invention also relates to procedures for the preparation of pharmaceutical compositions in which one or more compounds of the general formula (I) are mixed with suitable carriers and excipients (see above).

The invention is explained in more detail by the following embodiment examples.

EMBODIMENTS

Methods for the Analysis of Compounds

Analytical HPLC

For analytical reversed-phase HPLC, a HPLC system LC-10A of the company Shimadzu consisting of the subsystems CTO-10A column oven, LC-10ATvp pumps (2×), DGU-14A degasser, SIL-10Axl autoinjector, SCL-10Avp system controller, SPD-M10Avp photodiode array detector and a column 250/4.6 Nucleodur 100-5 C18 ec of the company Macherey-Nagel (Düren, Germany) and the associated software Shimadzu CLASS-VP, version 7.2.1 was used. Detection was performed at 220 nm. As eluent, water with 0.1% TFA (eluent A) and acetonitrile with 0.1% TFA (solvent B) were used at a flow rate of 1 ml/min and a linear gradient (increase of 1% B/min). The start conditions (% B) are each indicated in the respective syntheses.

Preparative HPLC

For preparative RP-HPLC, a HPLC system of the company Varian consisting of the subsystems Varian PrepStar model 218 preparative pumps (2×), Varian ProStar model 320 UV-Vis detector, Varian fraction collector model 701 and a column VP 250/32 Nucleodur 100-5 C8 ec of the company Macherey-Nagel (Düren, Germany) was used, as well as the associated Star software v. 6.0. Some separations were performed using a Prontosil C18 column (250/32, 120-5-C18-SH, Bischoff Chromatography). Detection was performed at 220 nm. As eluent, again water with 0.1% TFA (eluent A) and acetonitrile with 0.1% TFA (solvent B) was used at a flow rate of 20 ml/min and an appropriate gradient (increase of 1% B in 2 min).

Mass Spectrometry

Spectra were recorded on an instrument from Applied Biosystems (QTrap 2000) or an Autospec spectrometer of the company Micromass.

Abbreviations Used

4-AMBA 4-amidinobenzylamide

Boc tert.-butyloxycarbonyl

Chas cyclohexylaminosulfonyl

CKIBE chlorocarbonic acid isobutyl ester

DIPEA diisopropylethylamine

DCM dichloromethane

DMF N,N-dimethylformamide

EtOAc ethyl acetate

HATU 2-(7-aza-1H-benzotriazole-1-yl)-1,1,3,3-tetramethyluronium hexafluorophosphate methanaminium HPLC high performance liquid chromatography Me methyl MeCN acetonitrile MS mass spectroscopy NMM N-methylmorpholine Phe(4-$NO_2$) 4-nitrophenylalanine RT room temperature TFA trifluoroacetic acid TMS-Cl trimethylsilyl chloride Chemicals, solvents, reagents and amino acid derivatives used were purchased from the companies Aldrich, Fluka, Acros, Bachem, Iris Biotech, Peptech and Novabiochem.

EXAMPLE 1

Synthesis of Inhibitor 1

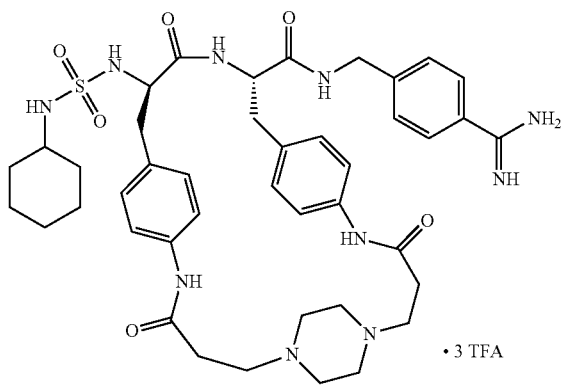 [SMILES: N=C(N)c1ccc(CNC(=O)[C@@H]2Cc3ccc(cc3)NC(=O)CCN3CCN(CCC(=O)Nc4ccc(cc4)C[C@@H](NS(=O)(=O)NC4CCCCC4)C(=O)N2)CC3)cc1]

1a) Chas-D-Phe(4-NO$_2$)—OH

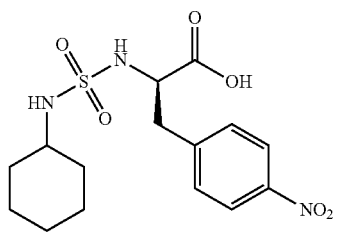 [SMILES: O=C(O)[C@@H](Cc1ccc([N+](=O)[O-])cc1)NS(=O)(=O)NC1CCCCC1]

2.0 g (9.52 mmol) of H-D-Phe(4-NO$_2$)—OH was suspended in 25 ml of dry DCM and 2.68 ml (20.93 mmol) of TMS-Cl and 3.64 ml (20.93 mmol) DIPEA added. The mixture was boiled for one hour under reflux, subsequently 2.54 g (12.85 mmol) cyclohexylsulfamoylchloride (G. White, G. Schulze, Liebigs Ann. Chem, 1969, 729, 40-51) was added portionwise within 35 min at 0° C., while the pH value was adjusted to 7-8 by adding a total of 2.23 ml (12.85 mmol) of DIPEA. The solution was stirred for 4 h on an ice bath and overnight at RT. The solvent was removed in vacuo and the brown, viscous residue was taken up in 5% KHSO$_4$ soln./EtOAc. The aqueous phase was extracted 2× with ethyl acetate. The combined organic phases were washed 2× with 5% KHSO$_4$ and 3× with saturated NaCl solution. The organic phase was dried with MgSO$_4$, filtered, and the solvent was removed in vacuo.

Yield: 3.095 g of pale brown amorphous solid (HPLC: 38.0 min, start at 10% B; MS: calc.: 371.12. found 372.17 [M+H]$^+$).

1b) Chas-D-Phe(4-NO$_2$)-Phe(4-NO$_2$)—OMe

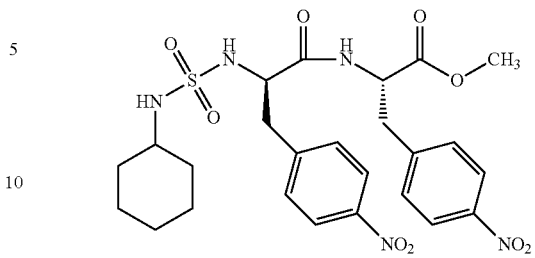

2.0 g (5.39 mmol) Chas-D-Phe(4-NO$_2$)—OH and 1.42 g (5.39 mmol) H-Phe(4-NO$_2$)—OMe.HCl were suspended in 30 ml of DMF and 2.82 g (5.39 mmol) of PyBOP and 2.81 ml (16.16 mmol) of DIPEA was added at 0° C. After 2 h of stirring at 0° C., the solvent was removed in vacuo and the brown residue resuspended in 5% KHSO$_4$ soln./EtOAc. The organic phase was washed 3× with 5%-KHSO$_4$ soln., 1× with sat. NaCl soln., 3× with sat. NaHCO$_3$-soln., and 3× with sat. NaCl soln., subsequently dried with MgSO$_4$, filtered, and the solvent was removed in vacuo.

Yield: 3.66 g of brown viscous oil (HPLC: 50.0 min, start at 10% B; calc.: 577.18 found: 600.29 [M+Na]$^+$).

1c) Chas-D-Phe(4-NH$_2$)-Phe(4-NH$_2$)—OMe

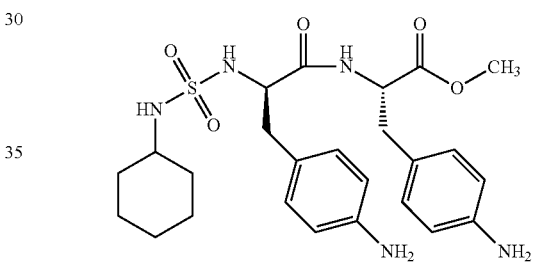

1.0 g (1.47 mmol) Chas-D-Phe(4-NO$_2$)-Phe(4-NO$_2$)—OMe was dissolved in 200 ml of 90% acetic acid, mixed with 101 mg of Pd—C, purged 3× and hydrogenated overnight with hydrogen. The catalyst was filtered off and the solvent removed in vacuo. The red, viscous oil was dissolved in 8 ml of 25% solvent B, filtered through a 0.2 μm filter and purified by prep. HPLC (start at 10% B). Fractions containing the product were combined, the solvent removed in vacuo, the residue dissolved in 40% t-butanol/water and lyophilized.

Yield: 328 mg of pale yellow, lyoph. substance (HPLC: 18.4 min, start at 10% B; calc.: 517.24. found: 518.13 [M+H]$^+$).

1d) N,N'-1,4-piperazine-dipropionic acid

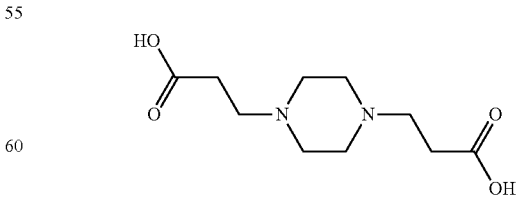

5 g (25.7 mmol) piperazine.6H$_2$O was dissolved in 140 ml 10% NaOH solution and 8.08 g (52.8 mmol) of 3-bromopropanoic acid was added. The yellow, clear solution was stirred overnight at RT. The solution was acidified with 37% HCl and the product then precipitated as a light yellow crystalline substance. The mixture was stored overnight at 4° C., the precipitate filtered off, washed with water and dried in vacuo.

Yield: 4.58 g of light yellow, crystalline substance (MS: calc.: 230.13. found 229.17 [M−H]⁻)

1e)

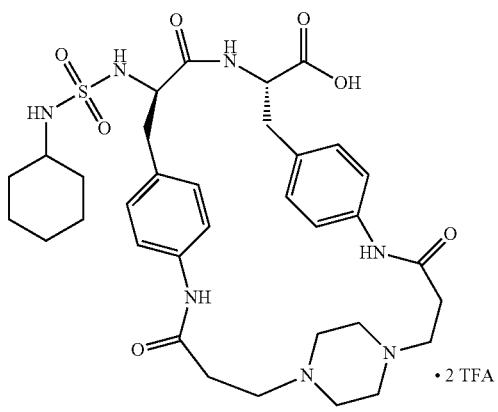 [SMILES: O=C1CCN2CCN(CCC(=O)Nc3ccc(cc3)C[C@@H](NS(=O)(=O)NC3CCCCC3)C(=O)N[C@H](C(=O)O)Cc3ccc(cc3)N1)CC2]

100 mg (0.193 mmol) Chas-D-Phe(4-NH$_2$)-Phe(4-NH$_2$)—OMe (1c) and 44.5 mg (0.193 mmol) of N,N'-1,4-piperazine-dipropionic acid was suspended in 50 ml of DMF and stirred on the ice bath. After addition of 202 mg (0.386 mmol) of PyBOP and 134.4 µl (0.773 mmol) of DIPEA, the mixture was stirred overnight at RT and the solvent subsequently removed in vacuo. The yellow oil was mixed with each 2 ml of ethanol and 1 N NaOH, the mixture was stirred for 2.5 h at RT and then neutralized with TFA. The solvent was removed in vacuo, the white residue was dissolved in 7 ml of 30% solvent B and purified by preparative HPLC (start at 15% B). The fractions containing the product were combined, the solvent removed in vacuo, the residue dissolved in 40% tert.-butanol/water and lyophilized.

Yield: 45.3 mg of white, lyoph. substance (HPLC: 23.9 min, start at 10% B, MS: calc.: 669.29. found: 670.24 [M+H]⁺).

1)

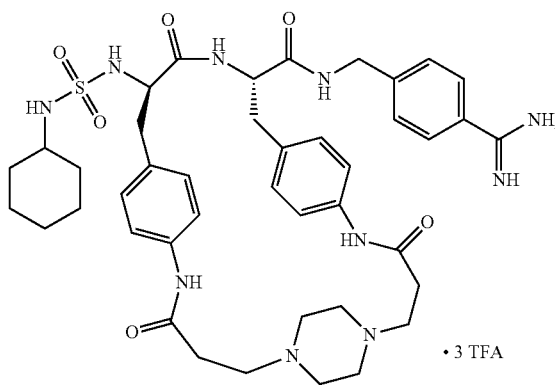

35 mg (0.0378 mmol) of product 1e was dissolved in 3 ml DMF and cooled to −15° C. After addition of 4.91 µl (0.0378 mmol) CKIBE and 12.5 µl (0.113 mmol) NMM, the mixture was stirred for 15 min and then 12.8 mg (0.0567 mmol) of 4-AMBA.2 HCl and 4.16 µl NMM were added. The mixture was stirred for one hour at −15° C. and overnight at RT and the solvent was subsequently removed in vacuo. The yellow residue was dissolved in 8 ml of 30% solvent B and purified by preparative HPLC (start at 15% B). Fractions containing the product were combined, the solvent removed in vacuo, the residue dissolved in 40% t-butanol/water and lyophilized.

Yield: 40.5 mg of white, lyoph. substance (HPLC: 21.7 min, start at 10% B, MS: calc.: 828.41. found: 829.59 [M+H]⁺, 415.47 [M+2H]⁺⁺).

EXAMPLE 2

Synthesis of Inhibitor 2

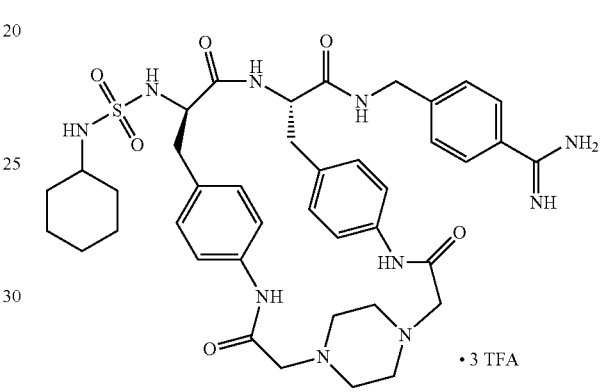

Inhibitor 2 was synthesized according to the strategy as described for the synthesis of inhibitor 1, only that in step 1e N,N'-piperazine-diacetic acid (Li Shen et al *Chem Eur J*, 2006, 12, 4393-4396) was used for the cyclization reaction.

Yield: 29 mg of white, lyoph. substance (HPLC: 21.1 min, start at 10% B, MS: calc.: 800.38. found: 801.38 [M+H]⁺).

EXAMPLE 3

Synthesis of Inhibitor 3

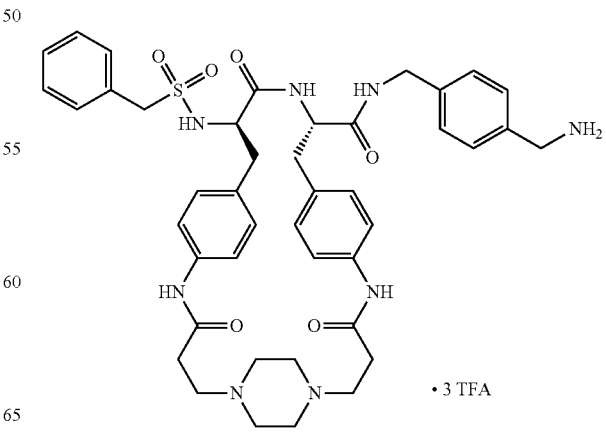

3a) BzIs-D-Phe(4-NO₂)—OH

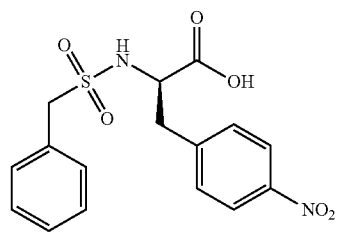 [SMILES: O=C(O)[C@@H](Cc1ccc([N+](=O)[O-])cc1)NS(=O)(=O)Cc1ccccc1]

5.0 g (23.8 mmol) H-D-Phe(4-NO₂)—OH (Peptech) was suspended in 50 ml of dry DCM and 6.5 ml (52.4 mmol) of TMS-Cl and 9.1 ml (52.4 mmol) of DIPEA was added. The mixture was boiled for 1 h under reflux and then cooled to 0° C. Subsequently, 5.02 g (26.3 mmol) benzenesulfonyl chloride was added in several portions within 1 h and the pH was adjusted to 8-9 by addition of 4.6 ml (26.4 mmol) of DIPEA. The solution was stirred at 0° C. for another hour and overnight at RT. The solvent was subsequently removed in vacuo and the brown residue was resuspended in 5% KHSO₄ soln./EtOAc. The aqueous phase was extracted 2× with EtOAc, and the combined organic phases were washed 3× with 5% KHSO₄ soln. and 3× with sat. NaCl soln., dried with MgSO₄, filtered, and the solvent was removed in vacuo.

The brown oil was dissolved in 250 ml of EtOAc, and 7.1 ml (35.5 mmol) of DCHA was added. The suspension was kept at 4° C. for several days. The brown crystals were filtered off, washed with EtOAc and diethyl ether, and dried in vacuo.

Yield: 8.2 g of light brown cryst. substance as DCHA salt (HPLC: 38.7 min, start at 10% B)

2.7 g of the DCHA salt was taken up in 5% KHSO₄ soln./EtOAc and the acidic aqueous phase was extracted 3× with EtOAc. The combined organic phases were washed 3× with sat. NaCl soln., dried with MgSO₄, filtered, and the solvent was removed in vacuo.

Yield: 1.8 g of light brown oil (HPLC: 38.7 min, start at 10% B, MS: calc.: 364.07. found: 363.1 [M+H]⁻).

3b) BzIs-D-Phe(4-NO₂)-Phe(4-NO₂)—OMe

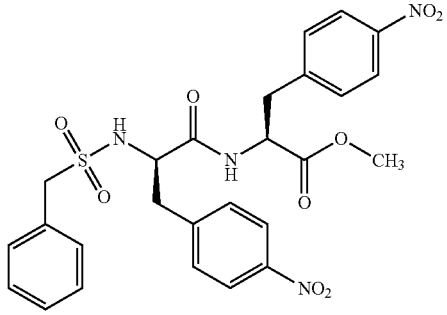 [SMILES: COC(=O)[C@H](Cc1ccc([N+](=O)[O-])cc1)NC(=O)[C@@H](Cc1ccc([N+](=O)[O-])cc1)NS(=O)(=O)Cc1ccccc1]

1.8 g (4.94 mmol) BzIs-D-Phe(4-NO₂)—OH (3a) and 1.29 g (4.94 mmol) H-Phe(4-NO₂)—OMe.HCl (Aldrich) were suspended in 30 ml of DMF and stirred on the ice bath. After addition of 2.57 g (4.94 mmol) of PyBOP and 1.72 ml (9.88 mmol) of DIPEA (pH 7-8), the mixture was stirred for 15 min at 0° C. and 3 h at RT. The solvent was removed in vacuo and the dark yellow oil was taken up in 5% KHSO₄ soln./EtOAc. The organic phase was washed 3× with 5% KHSO₄ soln., washed 1× with sat. NaCl soln., 3× with sat. NaHCO₃ soln., and 3× with sat. NaCl soln. The organic phase was dried with MgSO₄, filtered, and the solvent was removed in vacuo.

Yield: 3.55 g of brown amorphous residue with impurities (HPLC: 48.4 min, start at 10% B, MS: calc.: 570.57. found: 571.23 [M+H]⁺).

3c) BzIs-D-Phe(4-NH₂)-Phe(4-NH₂)—OMe

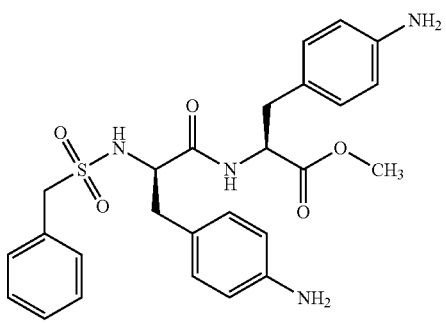

2.82 g BzIs-D-Phe(4-NO₂)-Phe(4-NO₂)—OMe (3b) was dissolved in 500 ml 90% acetic acid, zinc dust was added, the mixture was stirred at RT for 4 h and the solvent was then removed in vacuo. The yellow residue was suspended in MeCN/water (9/1, v/v), undissolved salts were removed by centrifugation, and the solvent was removed in vacuo. The residue was purified by prep. HPLC (start at 5% B). Fractions containing the product were combined; the solution was concentrated and lyophilized.

Yield: 2.02 g of light yellow, lyoph. substance (HPLC: 25.0 min, start at 1% B, MS: calc.: 510.61. found: 511.27 [M+H]⁺).

3d)

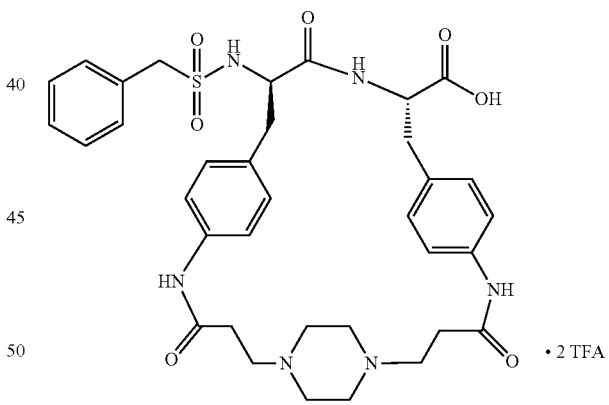

500 mg (0.979 mmol) BzIs-D-Phe(4-NH₂)-Phe(4-NH₂)—OMe (3c) and 225 mg (0.979 mmol) of N,N'-1,4-piperazine-dipropionic acid was suspended in 250 of DMF and stirred on the ice bath. After addition of 1.02 g (1.96 mmol) of PyBOP and 682 µl (3.92 mmol) of DIPEA, the mixture was stirred overnight and the solvent subsequently removed in vacuo. The dark red oil was dissolved with each 5 ml of ethanol and 1 N NaOH. The mixture was stirred at RT for 4 h and then neutralized with TFA. The solvent was removed in vacuo and the white residue was dissolved in 2×8 ml of 25% B and purified by preparative HPLC (start at 15% B). Fractions containing the product were combined, the solvent removed in vacuo, the residue dissolved in 40% t-butanol/water and lyophilized.

Yield: 204 mg of white, lyoph. solid (HPLC: 22.5 min, start at 10% B, MS: calc.: 690.28. found: 691.33 [M+H]$^+$, 713.36 [M+Na]$^+$).

3)

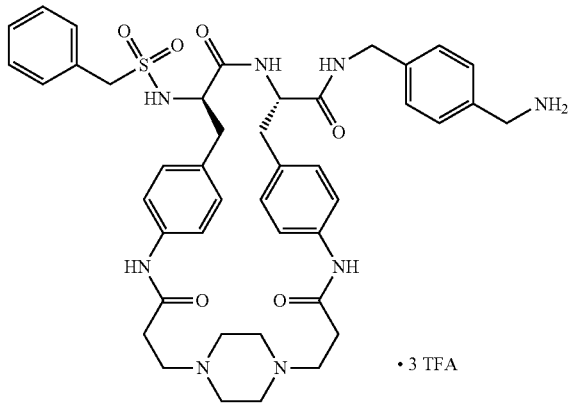 [SMILES: NCc1ccc(CNC(=O)[C@@H]2Cc3ccc(cc3)NC(=O)CCN3CCN(CCC(=O)Nc4ccc(cc4)C[C@@H](NS(=O)(=O)Cc4ccccc4)C(=O)N2)CC3)cc1]

• 3 TFA 100 mg (0.109 mmol) of compound 3d was dissolved in 4 ml of DMF and cooled to −15° C. After addition of 36 µl (0.327 mmol) of NMM and 15 µl (0.109 mmol) CKIBE, the solution was stirred for 15 min, followed by addition of 40 mg (0.169 mmol) of Boc-p-diaminoxylene and 12 µl (0.109 mmol) of NMM. The mixture was stirred for one hour at 0° C. and overnight at RT. The solvent was removed in vacuo, the residue was mixed with 1 ml 90% TFA and stirred for 2 h at RT. After removing the solvent in vacuo, the residue was dissolved in 8 ml of 30% B and purified by prep. HPLC (start at 10% B). Fractions containing the product were combined, the solvent was removed in vacuo and the residue dissolved in 80% t-butanol/water and lyophilized.

Yield: 39 mg of white, lyoph. solid (HPLC: 20.1 min, start at 10% B, MS: calc.: 808.37. found: 809.10 [M+H]$^+$, 405.34 [M+2H]$^{++}$/2).

EXAMPLE 4

Synthesis of Inhibitor 4

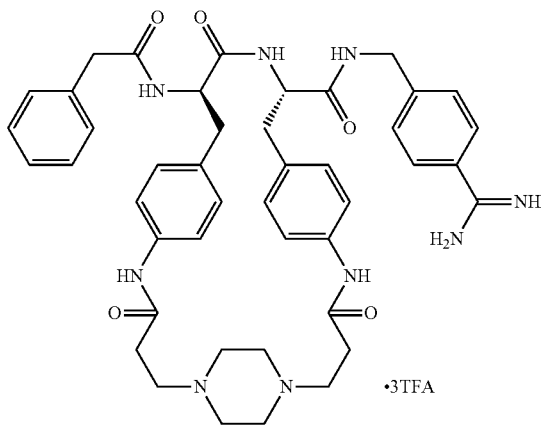 [SMILES: N=C(N)c1ccc(CNC(=O)[C@@H]2Cc3ccc(cc3)NC(=O)CCN3CCN(CCC(=O)Nc4ccc(cc4)C[C@@H](NC(=O)Cc4ccccc4)C(=O)N2)CC3)cc1]

•3TFA

4a) Boc-D-Phe(4-NO$_2$)-Phe(4-NO$_2$)—OMe

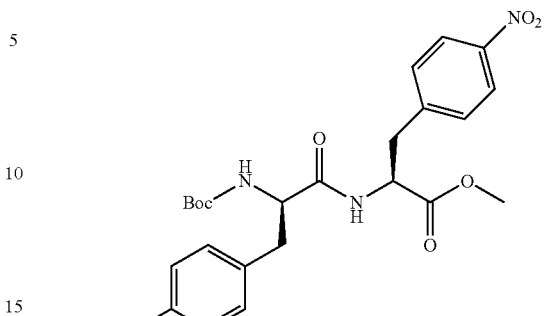

1.0 g (3.22 mmol) Boc-D-Phe(4-NO$_2$)—OH (Iris Biotech) and 0.84 g (3.22 mmol) H-Phe(4-NO$_2$)—OMe.HCl (Aldrich) were suspended in 25 ml of DMF and stirred on the ice bath. After addition of 1.66 g (3.22 mmol) of PyBOP and 1.67 ml (9.66 mmol) of DIPEA (pH 7-8), the mixture was stirred at 0° C. for 2.5 h. The solvent was removed in vacuo and the yellow oil was taken up in 5% KHSO$_4$ soln./EtOAc. The organic phase was washed 3× with 5% KHSO$_4$ soln., 1× with sat. NaCl soln., 3× with sat. NaHCO$_3$ soln. and 3× with sat. NaCl soln. The organic phase was dried with MgSO$_4$, filtered, and the solvent was removed in vacuo.

Yield: 1.76 g of yellow, amorphous residue with impurities (HPLC: 52.5 min, start at 10% B, MS: calc.: 516.19. found: 539.20 [M+Na]$^+$).

4b) Boc-D-Phe(4-NH$_2$)-Phe(4-NH$_2$)—OMe

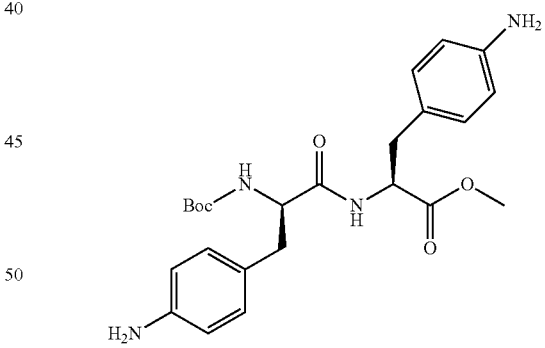

1.6 g (3.00 mmol) Boc-D-Phe(4-NO$_2$)-Phe(4-NO$_2$)—OMe (4a) was dissolved in 150 ml of 90% acetic acid. Then, 160 mg Pd—C was added, purged 3× and hydrogenated overnight at RT. After filtration of the suspension, the solvent was removed in vacuo. The residue was taken up in sat. NaHCO$_3$ soln./EtOAc and the organic phase was washed 3× with sat. NaHCO$_3$ soln. and 2× with sat. NaCl soln. The organic phase was dried with MgSO$_4$, followed by filtration and removal of the solvent in vacuo.

Yield: 1.36 g of a light brown amorphous solid (HPLC: 15.6 min, start at 10% B; calc.: 456.24. found: 479.21 [M+Na]$^+$).

4c)

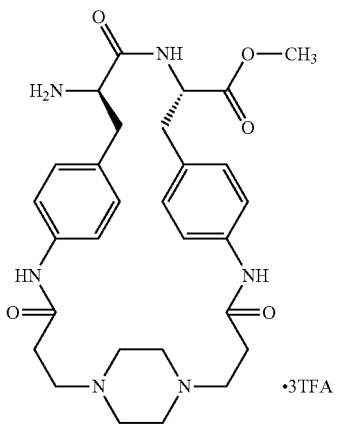 [SMILES: COC(=O)[C@@H]1Cc2ccc(cc2)NC(=O)CCN2CCN(CCC(=O)Nc3ccc(cc3)C[C@@H](N)C(=O)N1)CC2]

1.26 g (2.76 mmol) Boc-D-Phe(4-NH$_2$)-Phe(4-NH$_2$)—OMe (4b) and 630 mg (2.760 mmol) of N,N'-1,4-piperazine-dipropionic acid are suspended in 630 ml of DMF. After cooling at 0° C. for 5 min, 2.87 g (5.52 mmol) of PyBOP and 1.92 ml (11.04 mmol) DIPEA was added (pH 7-8) and the mixture stirred for 6 h. After HPLC control (incomplete conversion), another 1.15 g (2.210 mmol) of PyBOP and 768 µl (4.414 mmol) of DIPEA was added at 0° C. and the mixture was stirred for 1 h at 0° C. and overnight at RT. The solvent was removed in vacuo; the yellow oil mixed with 15 ml of TFA and allowed to stand for 1 h with occasional tilting. The product was precipitated with diethyl ether as TFA salt, the solvent removed and the product dried in vacuo. The reddish residue was dissolved in 20% solvent B and purified by prep. HPLC (start at 0% B). Fractions containing the product were combined, the solvent concentrated in vacuo and lyophilized.

Yield: 360 mg of white, lyoph. solid (HPLC: 11.3 min, start at 10% B; calc.: 550.29. found: 551.38 [M+H]$^+$, 573.35 [M+Na]$^+$).

4d)

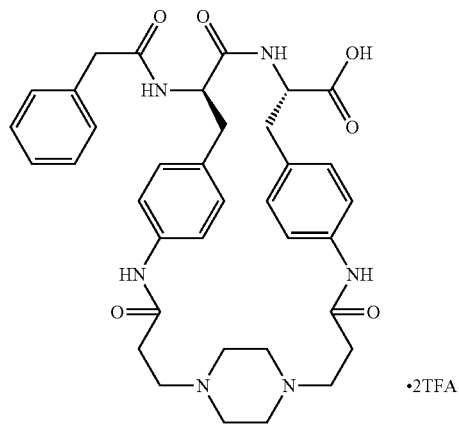 [SMILES: O=C1CCN2CCN(CCC(=O)Nc3ccc(cc3)C[C@@H](NC(=O)Cc3ccccc3)C(=O)N[C@H](C(=O)O)Cc3ccc(cc3)N1)CC2]

15.3 mg (0.112 mmol) of phenylacetic acid was dissolved in 3 ml of DMF and cooled to −15° C. After addition of 12.3 µl (0.112 mmol) of NMM and 14.6 µl (0.112 mmol) CKIBE, the solution was stirred for 15 min and then 100 mg (0.112 mmol) of compound 4c and 36.9 µl (0.336 mmol) of NMM was added. The mixture was stirred at −15° C. for 1 h and overnight at RT. The solvent was removed in vacuo. Each 2 ml of EtOH and 1 N NaOH was added to the residue and stirred for 3 h at RT. After neutralization with TFA, the solvent was removed in vacuo, the residue dissolved in 8 ml of 35% solvent B and purified by prep. HPLC (start at 15% B). Fractions containing the product were combined, the solvent removed in vacuo, the residue dissolved in 40% tert.-butanol/water and lyophilized.

Yield: 45 mg of white, lyoph. substance (HPLC: 21.4 min, start at 10% B, MS: calcd: 654.32. found 655.31 [M+H]$^+$, 677.09 [M+Na]$^+$).

4)

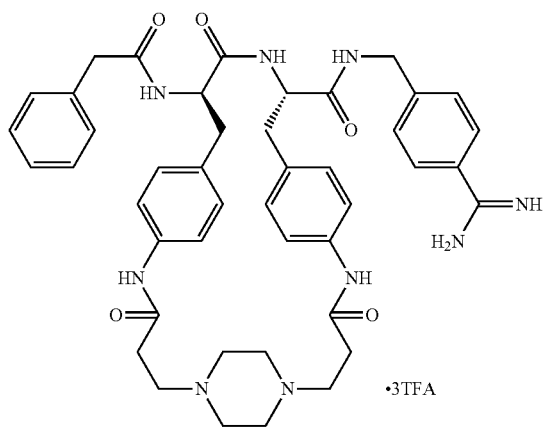 [SMILES: N=C(N)c1ccc(CNC(=O)[C@@H]2Cc3ccc(cc3)NC(=O)CCN3CCN(CCC(=O)Nc4ccc(cc4)C[C@@H](NC(=O)Cc4ccccc4)C(=O)N2)CC3)cc1]

40.1 mg (0.0453 mmol) of compound 4d was dissolved in 2 ml of DMF and cooled to −15° C. After addition of 15.0 µl (0.136 mmol) of NMM and 5.9 µl (0.0453 mmol) CKIBE, the solution was stirred for 15 min, followed by addition of 15.1 mg (0.0680 mmol) of 4-AMBA.2HCl and 5 µl (0.0453 mmol) of NMM. The mixture was stirred at −15° C. for 1 h and overnight at RT. The solvent was removed in vacuo, the residue dissolved in 8 ml of 30% solvent B and purified by prep. HPLC (start at 10% B). Fractions containing the product were combined, the solvent removed in vacuo, the residue dissolved in 40% t-butanol/water and lyophilized.

Yield: 16.5 mg white, lyoph. solid (HPLC: 19.3 min, start at 10% B, MS: calc.: 785.40. found: 786.30 [M+H]$^+$, 393.81 [M+2H]$^{++}$).

EXAMPLE 5

Synthesis of Inhibitor 5

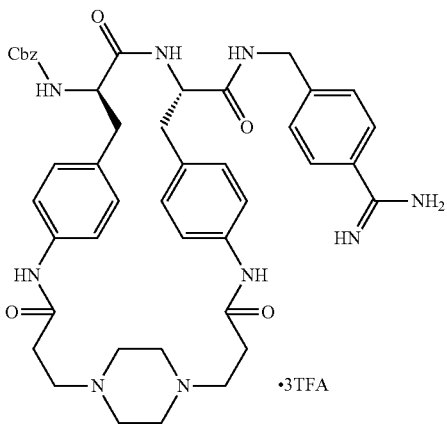 [SMILES: N=C(N)c1ccc(CNC(=O)[C@@H]2Cc3ccc(cc3)NC(=O)CCN3CCN(CCC(=O)Nc4ccc(cc4)C[C@@H](NC(=O)OCc4ccccc4)C(=O)N2)CC3)cc1]

5a)

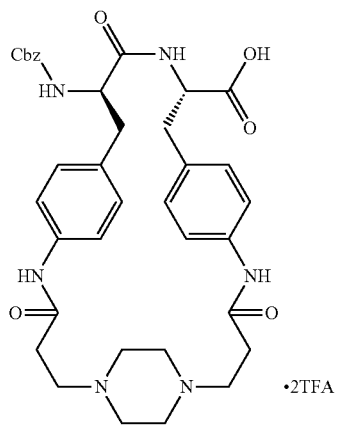 [SMILES: O=C1CCN2CCN(CCC(=O)Nc3ccc(cc3)C[C@@H](NC(=O)OCc3ccccc3)C(=O)N[C@H](C(=O)O)Cc3ccc(cc3)N1)CC2]

150 mg (0.168 mmol) of compound 4c was dissolved in 7 ml of MeCN and 57.3 µl (0.521 mmol) of NMM and cooled to 0° C. After addition of 46 mg (0.185 mmol) Cbz-OSu, the mixture was stirred for 1 hour at 0° C. and overnight at RT. The solvent was removed in vacuo and the residue was taken up in sat. NaHCO$_3$ solution/EtOAc. The organic phase was washed 3× with sat. NaHCO$_3$ solution and 3 times with sat. NaCl solution, followed by drying with MgSO$_4$ and removal of the solvent in vacuo. Each 5 ml of EtOH and 1 N NaOH was added to the yellow residue and stirred at RT for 3 h. The solvent was removed in vacuo, the residue dissolved in 8 ml of 30% solvent B and purified by prep. HPLC purified (start at 10% B). Fractions containing the product were combined, the solvent removed in vacuo, the residue dissolved in 40% t-butanol/water and lyophilized.

Yield: 51 mg of white, lyoph. solid (HPLC: 25.5 min, start at 10% B, MS: calc.: 670.31. found: 671.37 [M+H]$^+$, 693.39 [M+Na]$^+$).

5)

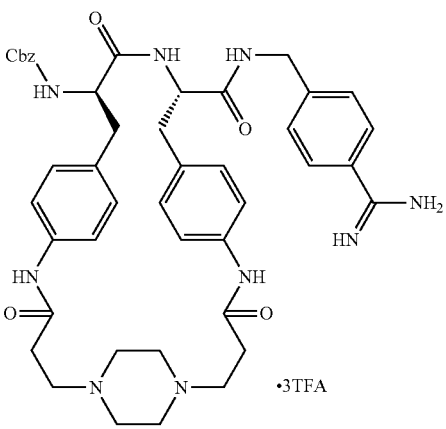 [SMILES: N=C(N)c1ccc(CNC(=O)[C@@H]2Cc3ccc(cc3)NC(=O)CCN3CCN(CCC(=O)Nc4ccc(cc4)C[C@@H](NC(=O)OCc4ccccc4)C(=O)N2)CC3)cc1]

40 mg (0.0445 mmol) of compound 5a was dissolved in 2 ml of DMF and cooled to −15° C. After addition of 14.7 µl (0.134 mmol) of NMM and 5.8 µl (0.0445 mmol) CKIBE, the solution was stirred for 15 min prior to addition of 14.8 mg (0.0668 mmol) of 4-AMBA.2HCl and 4.9 µl (0.0445 mmol) of NMM. The mixture was stirred at −15° C. for 1 h and overnight at RT. The solvent was removed in vacuo, the residue dissolved in 8 ml of 30% solvent B and purified by prep. HPLC (start at 10% B). Fractions containing the product were combined, the solvent removed in vacuo, the residue dissolved in 40% tert.-butanol/water and lyophilized. Yield: 21.1 mg of white, lyoph. solid (HPLC: 22.6 min, start at 10% B, calc.: 801.40. found: 802.50 [M+H]$^+$, 401.81 [M+2H]$^{++}$/2).

EXAMPLE 6

Synthesis of Inhibitor 6

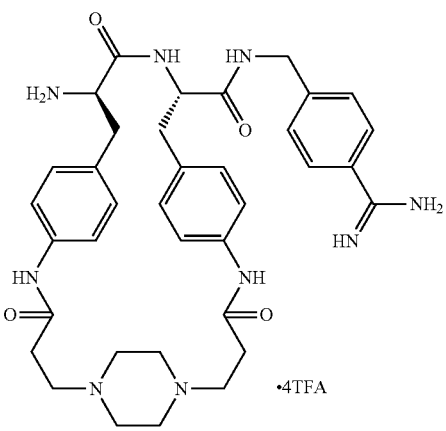 [SMILES: N=C(N)c1ccc(CNC(=O)[C@@H]2Cc3ccc(cc3)NC(=O)CCN3CCN(CCC(=O)Nc4ccc(cc4)C[C@@H](N)C(=O)N2)CC3)cc1]

6)

10 mg (0.00874 mmol) of compound 5 was mixed with 500 µl HBr/glacial acetic acid and allowed to stand for 1 h with occasional tilting. The product was precipitated with diethyl ether, dissolved in 8 ml of 20% solvent B and purified by preparative HPLC (start at 0% B). Fractions containing the product were combined, the solvent removed in vacuo, the residue dissolved in 40% tert.-butanol/water and lyophilized.

Yield: 8.2 mg of white, lyoph. solid (HPLC: 18.4 min, start at 1% B, MS: calc.: 667.36. found 668.2 [M+H]+).

EXAMPLE 7

Synthesis of Inhibitor 7

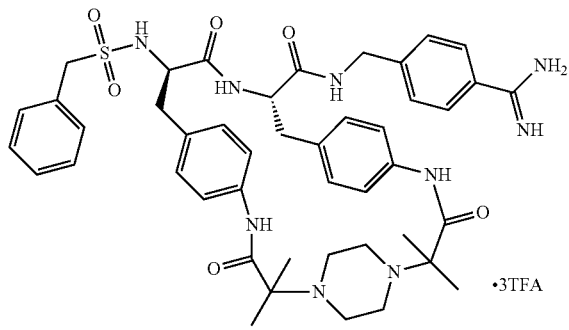 [SMILES: CC1(C)C(=O)Nc2ccc(cc2)C[C@@H](C(=O)NCc2ccc(C(=N)N)cc2)NC(=O)[C@H](NS(=O)(=O)Cc2ccccc2)Cc2ccc(cc2)NC(=O)C(C)(C)N2CCN1CC2]

7a) piperazine-N,N'-di-(2,2-dimethyl)acetic acid benzyl ester.2 TFA

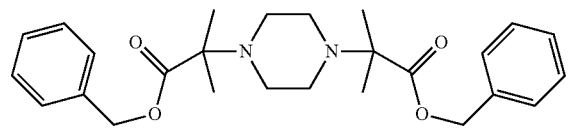 [SMILES: CC(C)(C(=O)OCc1ccccc1)N1CCN(C(C)(C)C(=O)OCc2ccccc2)CC1]

To 1.5 g (8.98 mmol) 2-bromo-2-methyl propionic acid, 934 µl (8.98 mmol) benzyl alcohol and 15.8 mg (0.084 mmol) of toluenesulphonic acid monohydrate, 4.5 ml toluene was added. The mixture was boiled for 18 h under reflux using a water separator. The solvent was removed in vacuo and the yellow oil taken up in 5% KHSO$_4$ soln./EtOAc The organic phase was extracted 3× with 5%-KHSO$_4$ soln., 1× with sat. NaCl soln., 3× with sat. NaHCO$_3$ soln. and 3× with sat. NaCl soln., washed, dried with MgSO$_4$, filtered, and the solvent was removed in vacuo (HPLC: 36.3 min, start at 30% B).

1.39 g (5.41 mmol) of the 2-bromo-2-methyl-propionic acid benzyl ester and 212 mg (2.46 mmol) of piperazine was dissolved in 30 ml of DMF, followed by addition of 1.43 g (6.15 mmol) Ag$_2$O. The mixture was stirred overnight at RT. After HPLC control, another 0.715 g (3.075 mmol) of Ag$_2$O was added and the mixture was stirred again overnight. The silver salts were filtered off and the solvent was removed in vacuo. The residue was dissolved and purified by prep. HPLC (start at 30% B)

Yield: 235.9 mg of a white amorphous solid (HPLC: 20.6 min, start at 30% B, MS: calc.: 438.25. found 439.10 [M+H]+).

7b) piperazine-N,N'-di-(2,2-dimethyl)acetic acid

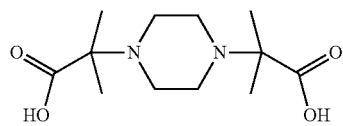 [SMILES: CC(C)(C(=O)O)N1CCN(C(C)(C)C(=O)O)CC1]

220 mg (0.330 mmol) of piperazine-N,N'-di-(2,2-dimethyl)acetic acid benzyl ester.2 TFA was dissolved in 80 ml of 90% acetic acid, and 22 mg Pd/C was added. After purging three times with hydrogen, the mixture was hydrogenated overnight. The suspension was filtered and the solvent removed in vacuo. The yellow residue was dissolved in a small amount of methanol and precipitated with diethyl ether.

Yield: 63.4 mg of white, cryst. substance (MS: calc.: 258.16. found: 259.00 [M+H]+).

7c)

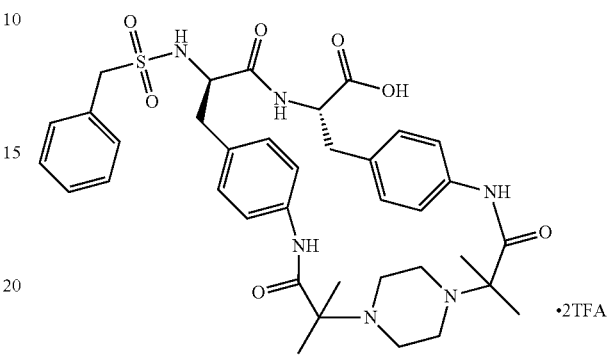

91 mg (0.178 mmol) of BzIs-D-Phe(4-NH$_2$)-Phe(4-NH$_2$)—OMe and 43 mg (0.166 mmol) of piperazine-N,N'-di-(2,2-dimethyl)acetic acid was suspended in 75 ml DMF and cooled on the ice bath. After addition of 165.3 mg (0.435 mmol) HATU and 182 µl (1.046 mmol) DIPEA, the mixture was stirred for 1 h at 0° C. and subsequently for 3 d at RT. After removal of the solvent in vacuo, the residue was dissolved in each 3 ml of EtOH and 1 N NaOH and stirred for 2.5 h at RT. The mixture was neutralized with TFA and the solvent removed in vacuo. The residue was dissolved and purified by prep. HPLC (start at 20% B).

Yield: 17 mg of white lyoph. substance (HPLC: 30.3 min, start at 10% B, MS: calc.: 718.31. found: 719.30 [M+H]+).

7)

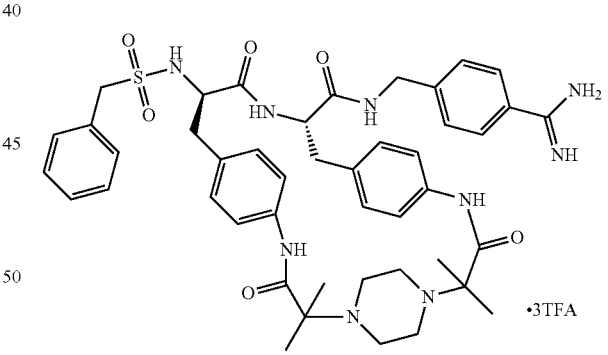

16 mg (0.0169 mmol) of compound 7c was dissolved in 500 µl DMF and cooled to −15° C. After addition of 5.6 µl (0.0507 mmol) of NMM and 2.2 µl (0.00169 mmol) CKIBE, the solution was stirred for 15 min and then treated with 5.6 mg (0.0250 mmol) of 4-AMBA.2HCl and 1.9 µl (0.0169 mmol) of NMM. The mixture was stirred for 1 h at −15° C. and overnight at RT. The solvent was removed in vacuo, the residue was dissolved in 8 ml 35% solvent B and purified by prep. HPLC (start at 15% B). Fractions containing the product were combined, the solvent removed in vacuo, the residue dissolved in 40% t-butanol/water and lyophilized.

Yield: 5.8 mg white lyoph. substance (HPLC: 26.2 min, start at 10% B, MS: calc.: 849.40. found: 850.50 [M+H]+).

EXAMPLE 8

Synthesis of Further Compounds

The following compounds were synthesized as described for the synthesis strategy for compound 7, except that in step a) instead of 2-bromo-2-methylpropionic acid, the compounds R-2-bromopropionic acid, S-2-bromopropionic acid or R/S-2-bromopropionic acid were used.

Inhibitor 8: (using R-2-bromopropionic acid in step a)

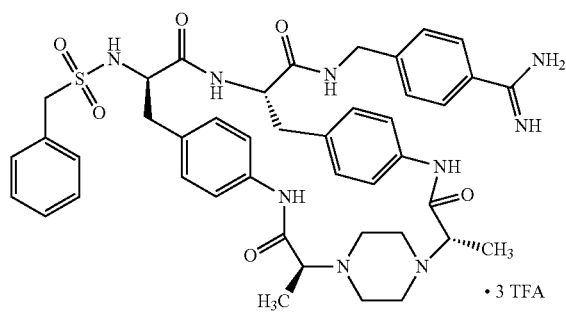 [SMILES: C[C@H]1C(=O)Nc2ccc(cc2)C[C@@H](C(=O)NCc2ccc(C(=N)N)cc2)NC(=O)[C@H](NS(=O)(=O)Cc2ccccc2)Cc2ccc(cc2)NC(=O)[C@H](C)N2CCN1CC2]

Yield: 37.8 mg of white lyoph. solid (HPLC: 23.4 min, start at 10% B, MS: calc.: 821.37. found: 822.5 [M+H]$^+$).

Inhibitor 9: (using S-2-bromopropionic acid in step a)

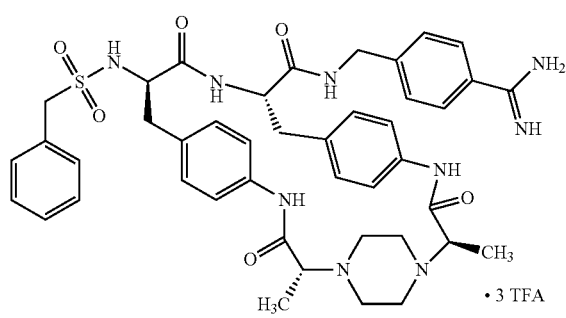 [SMILES: C[C@@H]1C(=O)Nc2ccc(cc2)C[C@@H](C(=O)NCc2ccc(C(=N)N)cc2)NC(=O)[C@H](NS(=O)(=O)Cc2ccccc2)Cc2ccc(cc2)NC(=O)[C@@H](C)N2CCN1CC2]

Yield: 39.6 mg of white lyoph. solid (HPLC: 23.6 min, start at 10% B, MS: calc.: 821.37. found: 822.5 [M+H]$^+$).

Inhibitor 10: (using racemic 2-bromopropionic acid in step a)

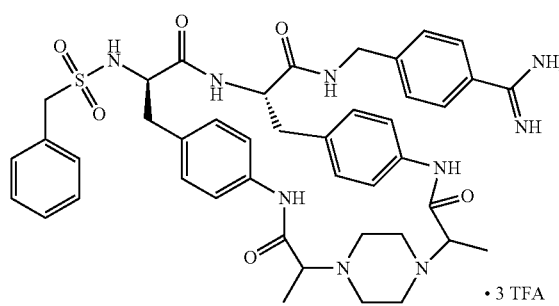

Yield: 103.7 mg of white lyoph. solid (HPLC: 21.1; 23.4; 23.6; 23.9 min, start at 10% B, MS: calc.: 821.37. found: 822.5 [M+H]$^+$).

Inhibitor 11: (This inhibitor was synthesized as described for the synthesis of inhibitor 5, only that N,N'''-piperazine-diacetic acid (Li Shen et al. Chem Eur J, 2006, 12. 4393-4396) was used for the cyclization reaction.)

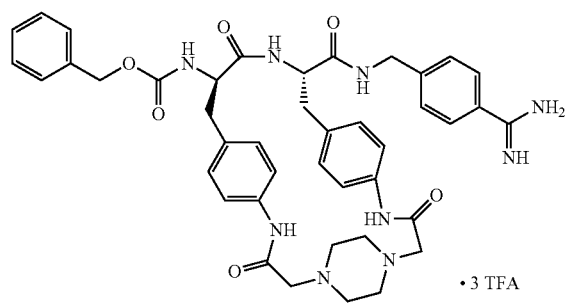 [SMILES: N=C(N)c1ccc(CNC(=O)[C@@H]2Cc3ccc(cc3)NC(=O)CN3CCN(CC3)CC(=O)Nc3ccc(cc3)C[C@@H](NC(=O)OCc3ccccc3)C(=O)N2)cc1]

Yield: 6 mg of white lyoph. solid (HPLC: 21.68 min, start at 10% B, MS: calc.: 773.36. found: 774.3 [M+H]$^+$).

Inhibitor 12: (This inhibitor was synthesized by removing the Cbz protecting group of the inhibitor 11 synthesized again with 32% HBr in acetic acid for 1 h at room temperature).

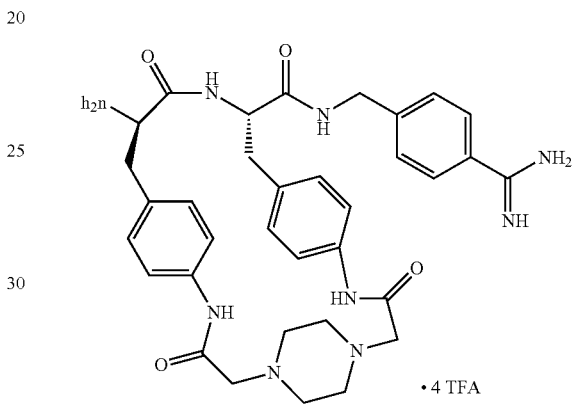

Yield: 14 mg of white lyoph. solid (HPLC: 19.09 min, start at 1% B, MS: calc.: 639.33. found: 320.86 [M+2H]$^{2+}$/2).

Inhibitor 13: (This inhibitor was synthesized by coupling of Boc-diaminobutane to intermediate 1e using PyBOP/DIPEA in DMF, followed by removal of the Boc protecting group with trifluoroacetic acid and construction of the guanidino group by reaction with each 3 equivalents of 1H-pyrazole-1-carboxamidine HCl and DIPEA in DMF at room temperature overnight, as well as final preparative HPLC).

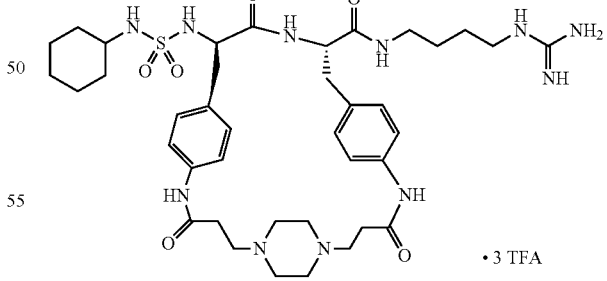

Yield: 12 mg of white lyoph. solid (HPLC: 21.0 min, start at 10% B, MS: calc.: 809.44. found: 810.47 [M+H]$^+$).

Inhibitor 14: (This inhibitor was synthesized by coupling of N,N-dimethylsulfamoyl chloride (Merck) to an intermediate analogous to compound 4c which however was cyclized with N,N'-piperazine-diacetic acid. After saponification of the methyl ester and coupling of 4-amidinobenzylamide, the final inhibitor was obtained and purified by preparative HPLC).

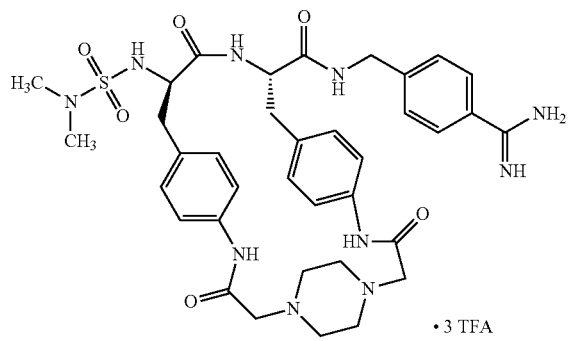 [SMILES: CN(C)S(=O)(=O)N[C@@H]1Cc2ccc(cc2)NC(=O)CN2CCN(CC2)CC(=O)Nc2ccc(cc2)C[C@@H](C(=O)NCc2ccc(C(=N)N)cc2)NC1=O]

Yield: 16 mg of white lyoph. solid (HPLC: 14.22 min, start at 10% B, MS: calc.: 746.33. found: 747.67 [M+H]$^+$).

Inhibitor 15: (This inhibitor was synthesized by coupling of N,N-dimethylsulfamoyl chloride (Merck) to compound 4c. After saponification of the methylester and coupling of 4-amidinobenzylamide, the final inhibitor was obtained and purified by preparative HPLC).

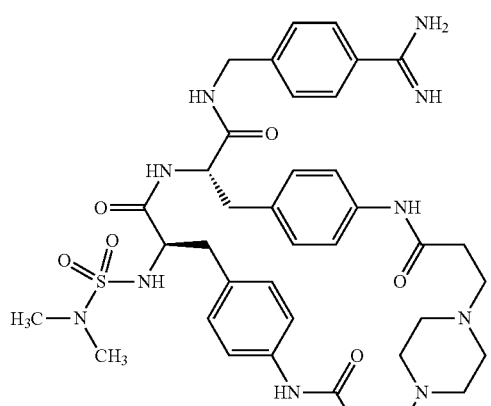

white, lyoph. solid (HPLC: 14.9 min, start at 10% B).

Inhibitor 16: (This inhibitor was synthesized as described for the synthesis of inhibitor 4, but instead of phenylacetic acid, in this case phenylpropionic acid was coupled by mixed anhydride procedure to intermediate 4c.)

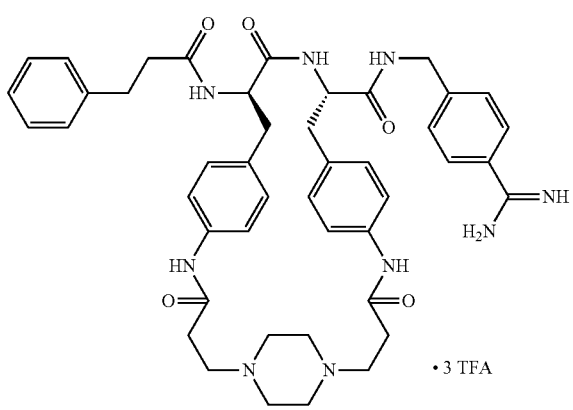 [SMILES: N=C(N)c1ccc(CNC(=O)[C@@H]2Cc3ccc(cc3)NC(=O)CCN3CCN(CCC(=O)Nc4ccc(cc4)C[C@@H](NC(=O)CCc4ccccc4)C(=O)N2)CC3)cc1]

white, lyoph. solid (HPLC: 20.2 min, start at 10% B).

Inhibitor 17: (This inhibitor was synthesized as described for inhibitor 4, but instead of phenylacetic acid, in this case phenylbutyric acid was coupled via the mixed anhydride procedure to intermediate 4c.)

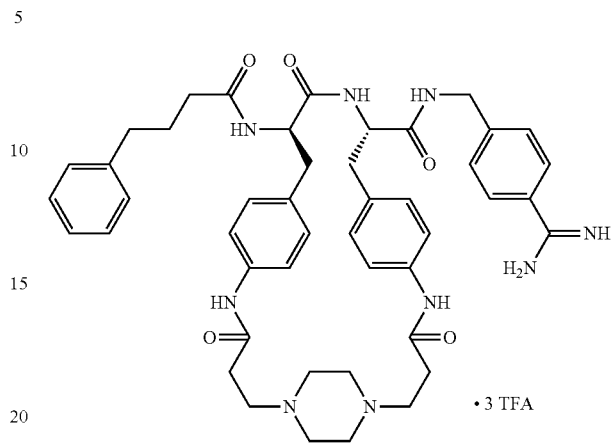

white, lyoph. solid (HPLC: 21.0 min, start at 10% B).

Example 9

Enzyme-kinetic Measurements

The determination of the inhibition constants for plasmin, PK, thrombin and factor, Xa was carried out with methods as described before (Stürzebecher et al., 1997) in a microplate reader (Multiscan Ascent of the company Thermo) at 405 nm. For these determinations, enzymes and substrates as summarized in Table 1 were used.

TABLE 1

| Enzymes and substrates used | |
|---|---|
| Enzyme | Substrate |
| Plasmin (human), Chromogenix, Specif. activity: 11 CU/mg | Tos-Gly-Pro-Lys-pNA (Chromozym PL) 4 mM (364 µM in the assay) 2 mM (182 µM in the assay) 1 mM (91 µM in the assay) |
| Plasma-Kallikrein (human), Enzyme Research South Bend | H-D-Pro-Phe-Arg-pNA (Haemochrom PK) 2 mM (182 µM in the assay) 1 mM (91 µM in the assay) 0.5 mM (45.5 µM in the assay) |
| Thrombin (bovine), 1425 IE/mg | CH$_3$SO$_2$-D-Cha-Gly-Arg-pNA (Pefachrome tPA) 2 mM (182 µM in the assay) 1 mM (91 µM in the assay) 0.5 mM (45.5 µM in the assay |
| Factor Xa (human) 2530PL, 200.35 IE/mg, Enzyme Research South Bend | CH$_3$OCO-D-CHA-Gly-Arg-pNA (Pefachrome FXa) 2 mM (182 µM in the assay) 1 mM (91 µM in the assay) 0.5 mM (45.5 µM in the assay) |

Measurement Approach:

200 µl 50 mM Tris×HCl buffer pH 8.0 (containing 0.154 M NaCl, 2% ethanol and the inhibitor in suitable concentration).

25 µl substrate start with 50 µl enzyme solution

The measurements were stopped by addition of 25 µl of 50% acetic acid, and K$_i$ values were calculated according to Dixon. The K$_i$ values are the mean value of at least two determinations.

Inhibitory Activity:

Inhibitors 1-10 inhibit plasmin inhibitors with $K_i$ values <15 nM, whereas thrombin, plasma kallikrein and factor Xa are inhibited with inhibition constants of >50 nM.

Concrete inhibition constants are given exemplarily in Table 2 for a few selected inhibitors.

TABLE 2

Inhibition of trypsin-like serine proteases plasmin, thrombin, factor Xa (FXa) and plasma kallikrein (PK) by selected inhibitors ($K_i$ in nM, nd = not determined).

| Inhibitor | $K_i$ (nM) | | | |
|---|---|---|---|---|
|  | Plasmin | PK | Thrombin | FXa |
| 1 | 0.052 | 600 | 17000 | 7400 |
| 2 | 0.32 | 319 | 16000 | 7900 |
| 3 | 1.24 | 6380 | 141000 | 78000 |
| 4 | 8.0 | 7920 | 41800 | 188400 |
| 5 | 0.77 | 6950 | 44000 | 47400 |
| 6 | 12.8 | 24500 | 60800 | 404500 |
| 7 | 2.2 | 77 | 620 | 1450 |
| 11 | 5.4 | 4640 | 46900 | 104200 |
| 13 | 3.5 | n.d. | n.d. | n.d. |
| 14 | 5.9 | 12000 | 4960 | 134400 |

The invention claimed is:

1. Compound according to formula (I)

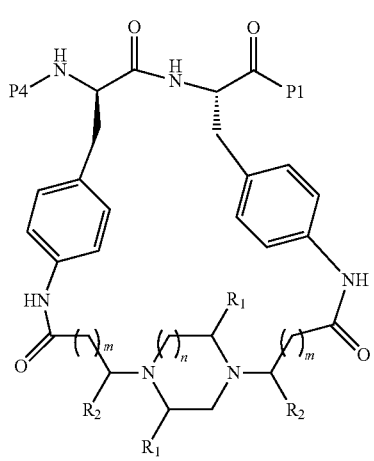

or a salt or a prodrug of said compound, characterized in that n equals 1 or 2, and m equals 0, 1 or 2, and $R_1$ is either H or a branched or unbranched alkyl having up to 3 carbon atoms, and $R_2$ is either H or a branched or unbranched alkyl having up to 5 carbon atoms or an aryl- or aralkyl residue with up to 7 carbon atoms, and P1 is one of the following groups:

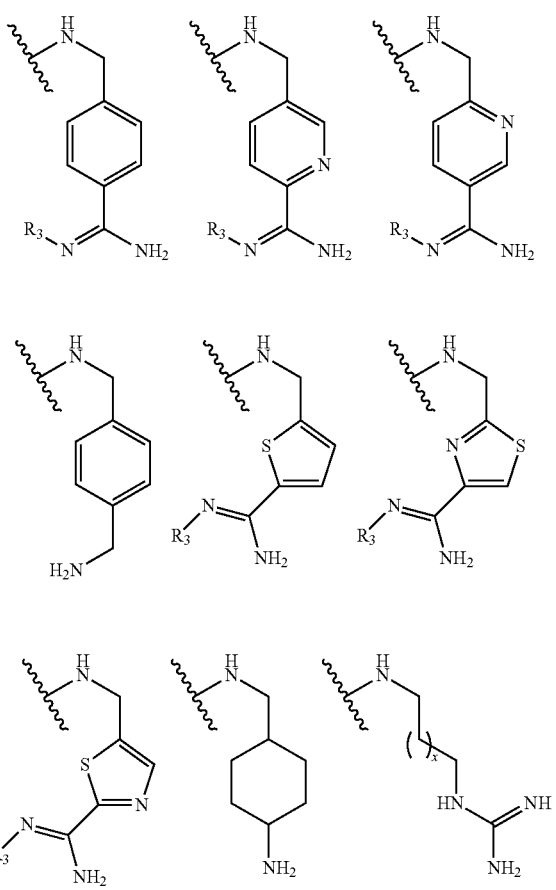

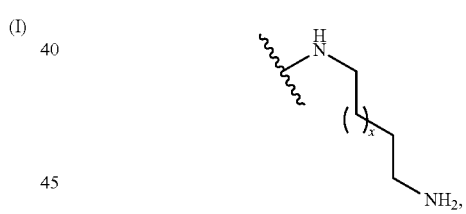

wherein $R_3$ can be H, OH, O—$CH_3$, $NH_2$, O—CO—$CH_3$ or CO—O—$(CH_2)_z$—$CH_3$ and z is an integer from 1 to 5, and x is an integer from 1 to 3, and P4 is either H, $SO_2$—$R_4$, $SO_2$—$NH_2$, $SO_2$—NH—$R_4$, $SO_2$—$N(R_4)_2$, CO—O—$R_4$, CO—$R_4$, $CH_2$—COOH, or $CH_2$—COOEt, wherein $R_4$ can be a branched or unbranched or cyclic alkyl group with 1 to 10 carbon atoms, or an aryl, a heteroaralkyl or aralkyl group with 6 to 10 carbon atoms, wherein the heteroaralkyl group may contain 1 to 3 heteroatoms chosen from N, S, or O, and wherein said alkyl, aryl, aralkyl and heteroaralkyl group can, if applicable, be substituted with 1 to 2 residues in arbitrary position which are chosen from the group of aminomethylene, cyano, $CF_3$, tetrazole, F, Cl, Br, COOH, COOEt, COOMe, methoxy, ethoxy, isopropoxy, methyl, ethyl, or isopropyl, and wherein the compound according to formula (I) is not

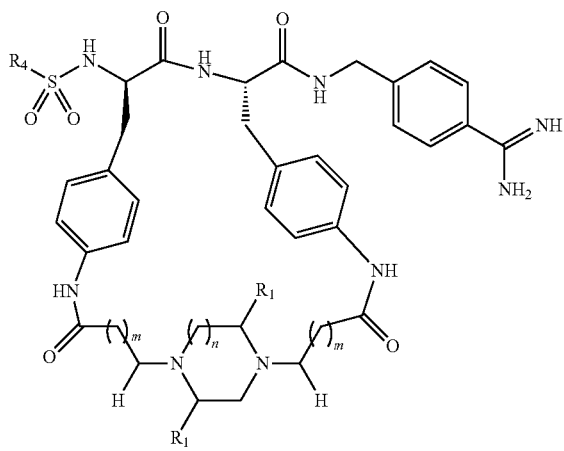

with $R_1$, $R_4$, m and n as defined above.

2. Compound according to claim 1, characterized in that $R_1$ is H.

3. Compound according to claim 1, characterized in that $R_2$ is H.

4. Compound according to claim 1, characterized in that P4 is H, $SO_2$—$NH_2$ or one of the following structures:

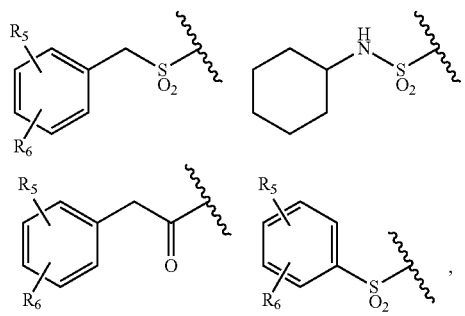

wherein $R_5$ and $R_6$ are, independently of one another, either H or aminomethylene, cyano, $OF_3$, tetrazole, F, Cl, Br, COOH, COOEt, COOMe, methoxy, ethoxy, isopropoxy, methyl, ethyl, or isopropyl.

5. Compound according to claim 4, wherein $R_5$ and $R_6$ are each independently H.

6. Compound according to claim 1, characterized in that P1 is selected from the following structures:

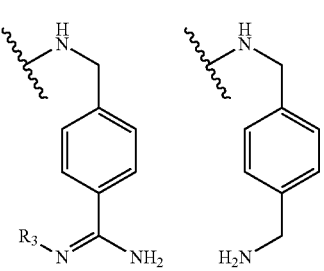

-continued

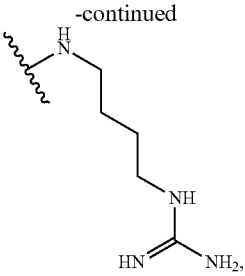

wherein $R_3$ is defined as before.

7. Compound according to claim 6, wherein $R_3$ is H.

8. Compound according to claim 1, characterized in that m equals 0 or 1.

9. Compound according to claim 1, characterized in that it can have the following structures:

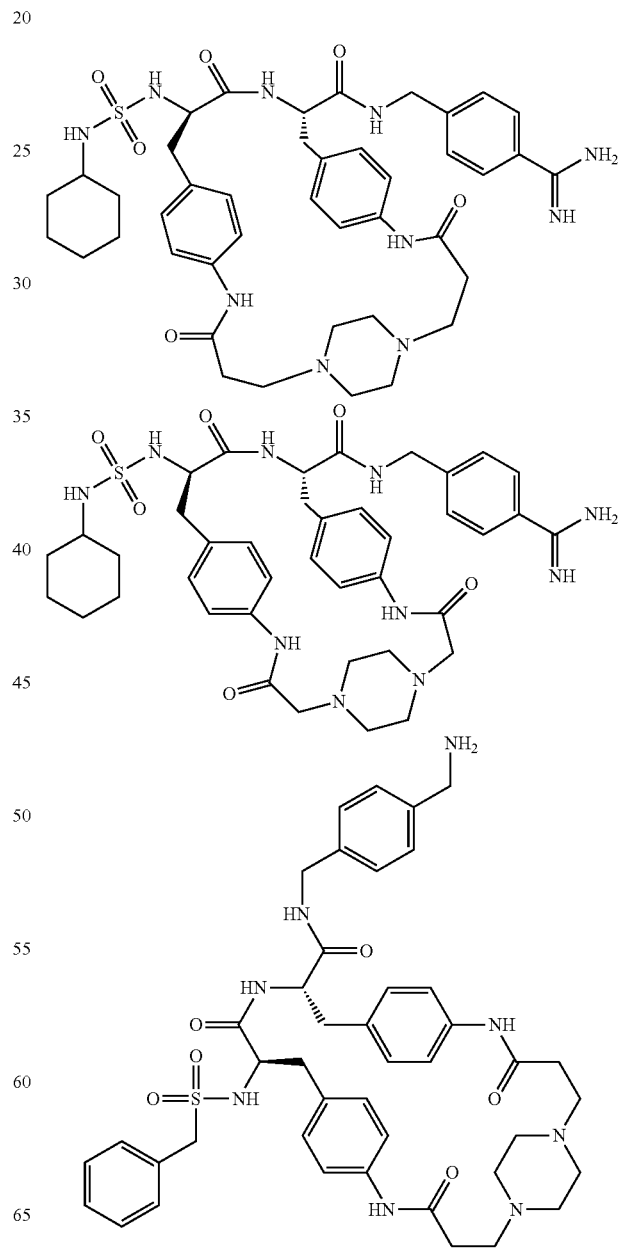

37
-continued
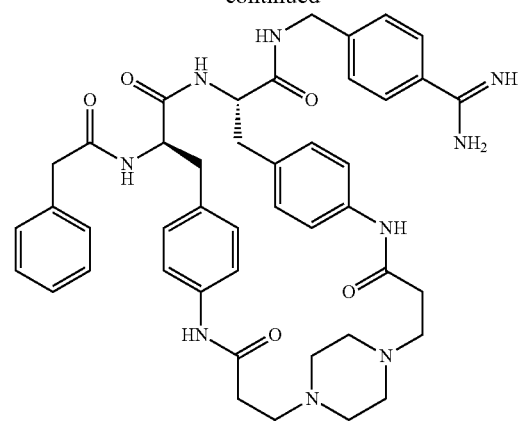
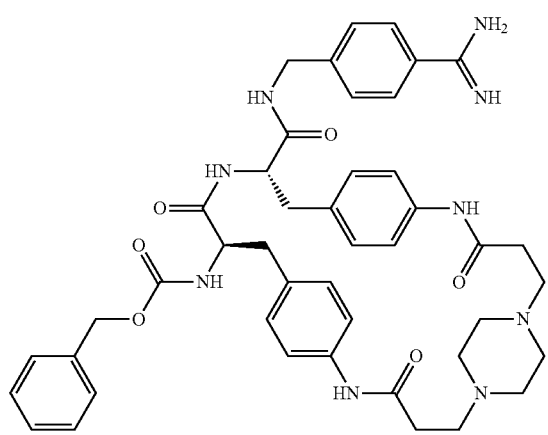
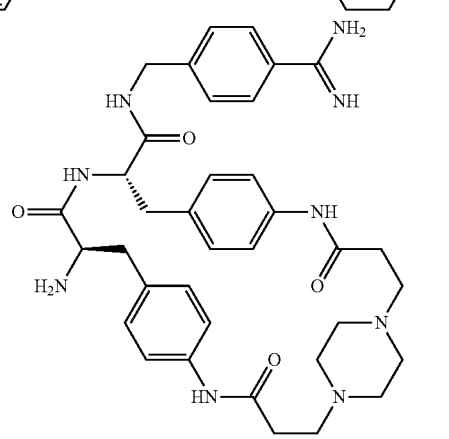
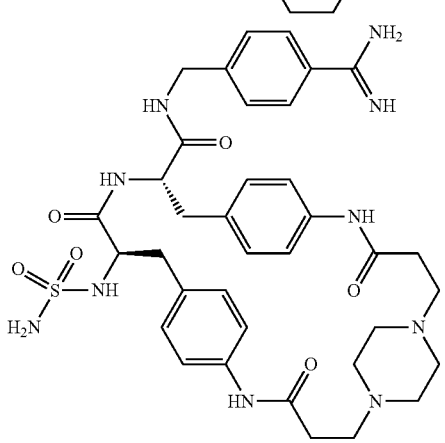
38
-continued
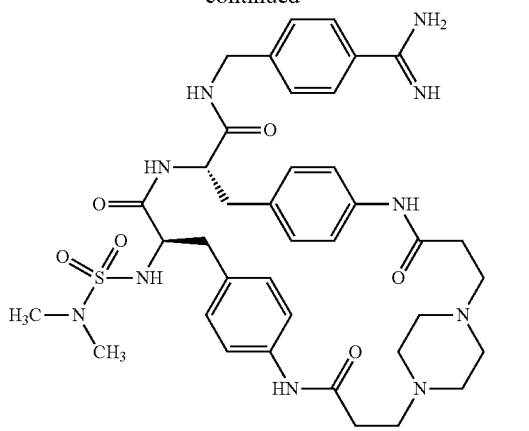
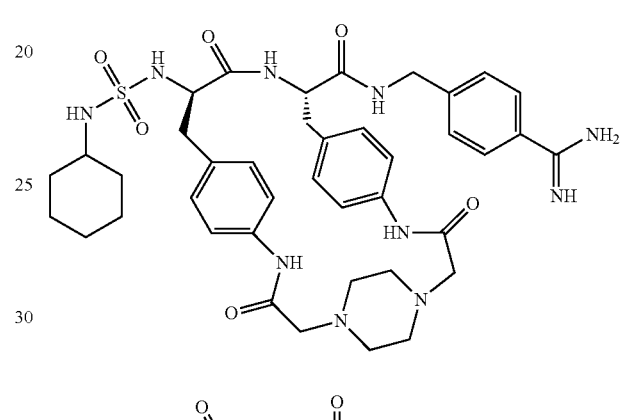
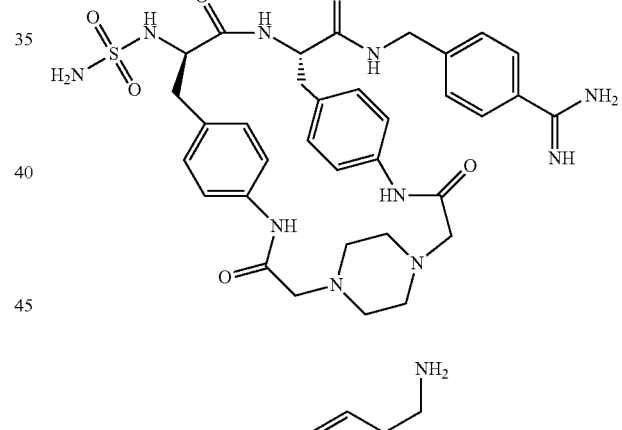
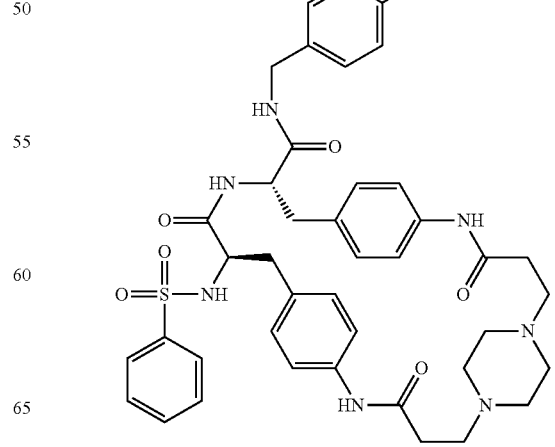

39
-continued
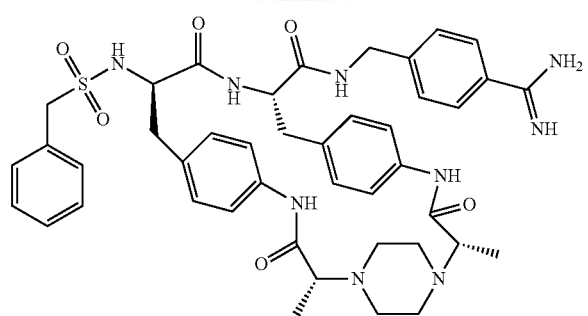
40
-continued
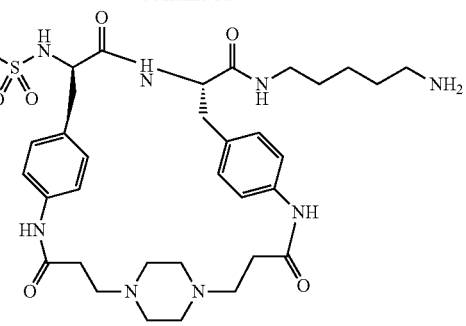
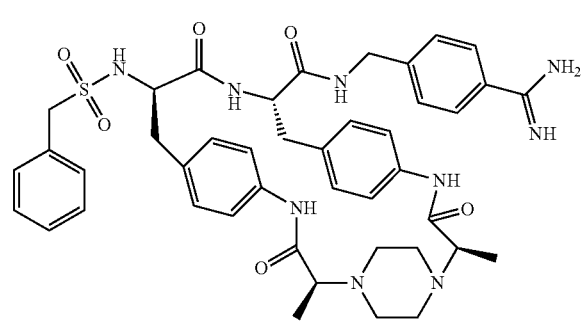
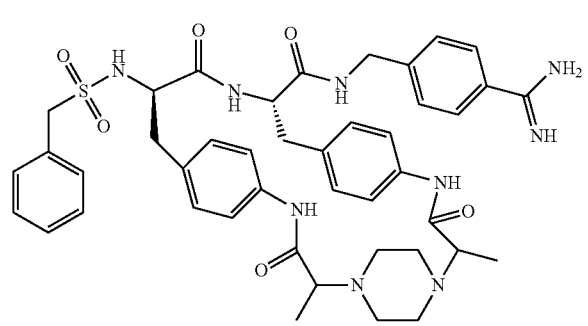
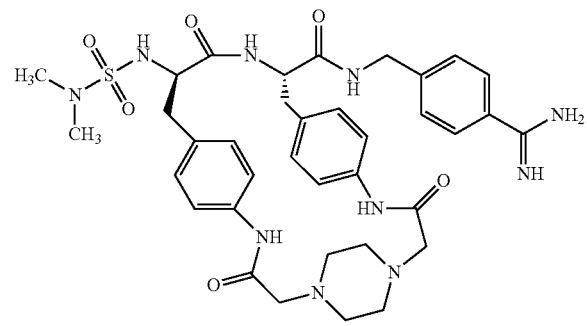
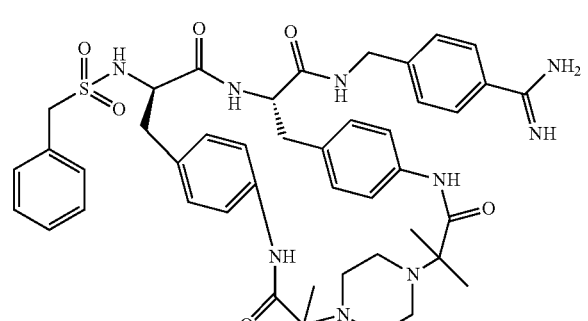
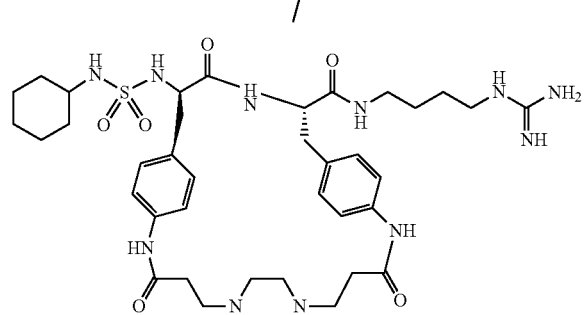
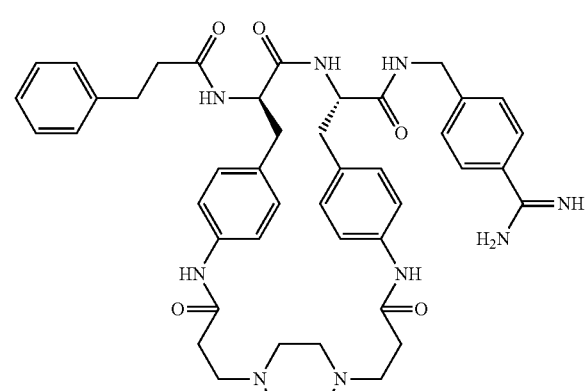

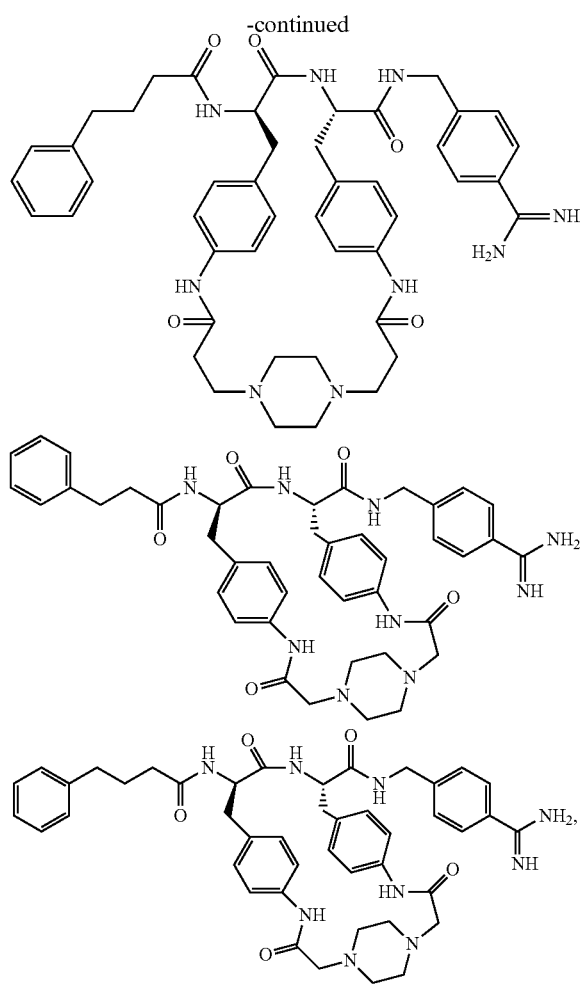

wherein the basic and, if applicable, existing acidic groups are present in a physiologically acceptable salt form.

10. A medicament, comprising at least one compound according to claim 1.

11. A medicament according to claim 10, characterized in that it is used in the form of a tablet, a dragee, a capsule, a pellet, a suppository, a solution, a juice, an emulsion or suspension, a globule, a styli, an aerosol, a powder, a paste, a cream or an ointment.

12. A medicament according to claim 10, characterized in that it is used in the form of an injection or an infusion solution of eye, nose or ear drops.

13. A method of reducing blood loss in a case of hyperfibrinolytic conditions by administering the compound of claim 1 or a medicament comprising at least said compound to a human or animal.

14. A method of either reducing blood loss during surgery, alleviating menstrual bleeding, alleviating bleeding during tooth extraction, alleviating bleeding gums, or treating hemophilia by administering the compound according to claim 1 or a medicament comprising at least said compound to a human or animal.

15. A method of inhibiting plasmin by in vitro applications comprising administering the compound of claim 1 in the in vitro application for inhibiting plasmin.

16. A method of treating arthritis or proliferative vitreoretinopathy by administering the compound of claim 1 or a medicament comprising at least said compound to a human or animal.

17. A method of using an antidote for thrombolytic therapy with plasmin or plasmin activators comprising using the compound according to claim 1 or a medicament comprising at least said compound as said antidote.

18. A method of inhibiting plasmin by in vitro applications comprising administering the compound of claim 1 in the in vitro application for inhibiting plasmin.

* * * * *